(12) United States Patent
Nemunaitis et al.

(10) Patent No.: US 9,132,146 B2
(45) Date of Patent: *Sep. 15, 2015

(54) FURIN-KNOCKDOWN AND GM-CSF-AUGMENTED (FANG) CANCER VACCINE

(75) Inventors: John J. Nemunaitis, Cedar Hill, TX (US); Neil Senzer, Dallas, TX (US); Phillip B. Maples, Pilot Point, TX (US); Donald Rao, Dallas, TX (US)

(73) Assignee: GRADALIS, INC., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,823

(22) Filed: Dec. 20, 2010

(65) Prior Publication Data

US 2011/0262408 A1 Oct. 27, 2011

Related U.S. Application Data

(60) Provisional application No. 61/289,681, filed on Dec. 23, 2009, provisional application No. 61/309,777, filed on Mar. 2, 2010.

(51) Int. Cl.
| | |
|---|---|
| *C12N 15/11* | (2006.01) |
| *C07H 21/04* | (2006.01) |
| *A61K 31/7088* | (2006.01) |
| *A61K 31/7105* | (2006.01) |

(52) U.S. Cl.
CPC ......... *A61K 31/7088* (2013.01); *A61K 31/7105* (2013.01)

(58) Field of Classification Search
None
See application file for complete search history.

(56) References Cited

U.S. PATENT DOCUMENTS

| | | | | |
|---|---|---|---|---|
| 8,119,395 | B1* | 2/2012 | Weiner et al. | 435/320.1 |
| 2007/0179113 | A1* | 8/2007 | Bauzon et al. | 514/44 |
| 2007/0224194 | A1* | 9/2007 | McColl et al. | 424/139.1 |
| 2008/0269474 | A1* | 10/2008 | Rao | 536/24.5 |
| 2010/0087625 | A1* | 4/2010 | Peel et al. | 530/350 |
| 2011/0045534 | A1* | 2/2011 | Cheung et al. | 435/69.6 |

FOREIGN PATENT DOCUMENTS

| | | |
|---|---|---|
| CA | 1 341 197 C | 3/2001 |
| CN | 101120086 A | 2/2008 |
| WO | 2006/086838 A1 | 8/2006 |
| WO | 2011/079070 A1 | 6/2011 |

OTHER PUBLICATIONS

Borrello et al., GM-CSF-based cellular vaccines: a review of the clinical experience, Cytokine & Growth Factor Reviews, 2002, vol. 13, pp. 185-193.*

Zeng et al., Structural requirements for pre-microRNA binding and nuclear export by Exportin 5, 2004, Nucleic Acids Research, vol. 32, pp. 4776-4785.*
Lagos-Quintana et al., Identification of novel genes coding for small expressed RNAs, 2001, Science, vol. 294, pp. 853-858.*
John Nemunaitis, Vaccines in cancer: GVAX®, a GM-CSF gene vaccine, 2005, Expert Review of Vaccines, vol. 4, pp. 259-274.*
Bassi et al., Furin inhibition results in absent or decreased invasiveness and tumorigenicity of human cancer cells, 2001, PNAS, vol. 98, pp. 10326-10331.*
Chapman et al., Effect of intron A from human cytomegalovirus (Towne) immediate-early gene on heterologous expression in mammalian cells, 1991, Nucleic Acids Research, vol. 19, pp. 3979-3986.*
Rana, Shushan, et al., "Stathmin 1: A Novel Therapeutic Target for Anticancer Activity," Expert Reviews, (2008), pp. 1461-1470.
Rao, DD, et al., "Enhanced Target Gene Knockdown by a Bifunctional shRNA: A Novel Approach of RNA Interference," Cancer Gene Therapy, (2010), 12 pages.
Romero, Pedro, "Current State of Vaccine Therapies in Non-Small-Cell Lung Cancer," Clinical Lung Cancer, (2008), vol. 9, Suppl. 1, pp. S28-S36.
Schalken, Jack A., et al., "fur Gene Expression as a Discriminating Marker for Small Cell and Nonsmall Cell Lung Carcinomas," J. Clin. Invest., Dec. 1987, vol. 80, pp. 1545-1549.
Takeuchi, Masaru, et al., "TGF-B Promotes Immune Deviation by Altering Accessory Signals of Antigen-Presenting Cells," J. Immunol., (1998), 160:1589-1597.
Thomas, Dori A., et al., "TGF-B Directly Targets Cytotoxic T Cell Functions During Tumor Evasion of Immune Surveillance," Cancer Cell, Nov. 2005, vol. 8, pp. 369-380.
Thomas, Gary, "Furin at the Cutting Edge: From Protein Traffic to Embryogenesis and Disease," Nat. Rev. Mol. Cell Biol., (Oct. 2002), 3(10):753-766.
Tong, Alex W., et al., "Intratumoral Injection of INGN 241, a Nonreplicating Adenovector Expressing the Melanoma-Differentiation Associated Gene-7 (mda-7/IL24): Biologic Outcome in Advanced Cancer Patients," Molecular Therapy, Jan. 2005, vol. 11, No. 1, pp. 160-172.
Tsunawaki, Shohko, et al., "Deactivation of Macrophages by Transforming Growth Factor-B," Jul. 21, 1988, vol. 334, pp. 260-262.
Wick, Wolfgang, et al., "Transforming Growth Factor-B: A Molecular Target for the Future Therapy of Glioblastoma," Current Pharmaceutical Design, (2006), 12:341-349.
Yamaguchi, Yasunori, et al., "Contrasting Effects of TGF-B1 and TNF-a on the Development of Dendritic Cells from Progenitors in Mouse Bone Marrow," Stem Cells, (1997), 15:144-153.

(Continued)

*Primary Examiner* — Dana Shin
(74) *Attorney, Agent, or Firm* — Chalker Flores, LLP; Edwin S. Flores

(57) ABSTRACT

Compositions and methods for cancer treatment are discloses herein. More specifically the present invention describes an autologous cancer vaccine genetically modified for Furin knockdown and GM-CSF expression. The vaccine described herein attenuates the immunosuppressive activity of TGF-β through the use of bi-functional shRNAs to knock down the expression of furin in cancer cells, and to augment tumor antigen expression, presentation, and processing through expression of the GM-CSF transgene.

7 Claims, 21 Drawing Sheets

(56) References Cited

OTHER PUBLICATIONS

Yuan, Bingbing, et al., "siRNA Selection Server: an Automated siRNA Oligonucleotide Prediction Server," Nucleic Acids Research, (2004), vol. 32, pp. W130-W134.

International Search Report and Written Opinion for PCT/US2010/061344, dated Feb. 20, 2011, 12 pages.

Maples, Phillip B., et al., "FANG Vaccine: Autologous Tumor Cell Vaccine Genetically Modified to Express GM-CSF and Block Production of Furin," Bio Processing Journal, Winter 2009/2010, vol. 8, No. 4, 12 pages.

Scamuffa, Nathalie, et al., "Selective Inhibition of Proprotein Convertases Represses the Metastatic Potential of Human Colorectal Tumor Cells," The Journal of Clinical Investigation, Jan. 2008, vol. 118, No. 3, pp. 352-363.

Ardeshna, Kirit M., et al., "The PI3 Kinase, p38 SAP Kinase, and NF-kB Signal Transduction Pathway Involved in the Survival and Maturation of Lipopolysaccharide-Stimulated Human Monocyte—Derived Dendritic Cells," Blood, Aug. 1, 2000, vol. 96, No. 3, pp. 1039-1046.

Arteaga, Carlos L., "Inhibition of TGFB Signaling in Cancer Therapy," Current Opinion in Genetics & Development, (2006), 16:30-37.

Ashcroft, Gillian S., "Bidirectional Regulation of Macrophage Function by TGF-B," Microbes and Infection, 1999, pp. 1275-1282.

Azuma-Mukal, Asuka, et al., "Characterization of Endogenous Human Argonautes and their miRNA Partners in RNA Silencing," PNAS, Jun. 10, 2008, vol. 105, No. 23, pp. 7964-7969.

Banchereau, Jacques, et al., "Immunobiology of Dendritic Cells," Annu. Rev. Immunol., (2000), 18:767-811.

Bassi, Daniel E., et al., "Elevated Furin Expression in Aggressive Human Head and Neck Tumors and Tumor Cell Lines," Molecular Carcinogenesis, (2001), 31:224-232.

Bassi, Daniel E., et al., "The Proprotein Convertases Furin and PACE4 Play a Significant Role in Tumor Progression," Molecular Carcinogenesis, (2000), 28:63-69.

Bommireddy, Ramireddy, et al., "TGFB1 and Treg Cells: Alliance for Tolerance," Trends Mol. Med., Nov. 13, 2007, 13(11):492-501.

Border, Wayne A., et al., "Transforming Growth Factor-B in Disease: The Dark Side of Tissue Repair," J. Clin. Invest., Jul. 1992, vol. 90, 7 pages.

Burghardt, Isabel, et al., "Pirfenidone Inhibits TGF-B Expression in Malignant Glioma Cells," Biochemical and Biophysical Research Communications, (2007), 354:542-547.

Cheng, Min, et al., "Pro-Protein Convertase Gene Expression in Human Breast Cancer," Int. J. Cancer, (1997), 71:966-971.

Dranoff, Glenn, et al., "Vaccination with Irradiated Tumor Cells Engineered to Secrete Murine Granulocyte-Machrophage Colony-Stimulating Factor Stimulates Potent, Specific, and Long-Lasting Anti-Tumor Immunity," Proc. Natl. Acad. Sci., Apr. 1993, vol. 90, pp. 3539-3543.

Du Caigan, et al., "Mechanism of Inhibition of LPS-Induced IL-12p40 Production by IL-10 and TGF-Bin ANA-1 Cells," Journal of Leukocyte Biology, Jul. 1998, vol. 64, pp. 92-97.

Fakhrai, H., et al., "Phase I Clinical Trial of a TGF-B Antisense-Modified Tumor Cell Vaccine in Patients with Advanced Glioma," Cancer Gene Therapy, (2006), 9 pages.

Fantini, Massimo, et al., "Cutting Edge: TGF-B Induces a Regulatory Phenotype in CD4 + CD25-T Cells Through Foxp3 Induction and Down Regulation of Smad7," J. Immunol., (2004), 172:5149-5153.

Fogel-Petrovic, Mirjana, et al., "Physiological Concentrations of Transforming Growth Factor B1 Selectively Inhibit Human Dendritic Cell Function," International Immunopharmacology, (2007), 7:1924-1933.

Friedman, E., et al., "High Levels of Transforming Growth Factor Beta 1 Correlate with Disease Progression in Human Colon Cancer," Cancer Eipdemiol Biomarkers Prev., (1995), pp. 549-554.

Funston, Garth M., et al., "Expression of Heterologous Genes in Oncolytic Adenoviruses Using Picornavital 2A Sequences that Trigger Ribosome Skipping," Journal of General Virology, (2008), 89:389-396.

Geissmann, Frederic, et al., "TGF-B1 Prevents the Noncognate maturation of Human Dendritic Langerhans Cells," J. Immunol., (1999), 162:4567-4575.

Hege, Kristen M., et al., "GM-CSF Gene-Modified Cancer Cell Immunotherapies: Of Mice and Men," International Reviews of Immunology, (2006), 25:321-352.

Henrich, Stefan, et al., "The Crystal Structure of the Proprotein Processing Proteinase Furin Explains its Stringent Specificity," Jul. 2003, vol. 10, No. 7, pp. 520-527.

Hodi, F. Stephen, et al., "Immunologic and Clinical Effects of Antibody Blockade of Cytotoxic T Lymphocyte-Associated Antigen Previously Vaccinated Cancer Patients," PNAS, Feb. 26, 2008, vol. 105, No. 8, pp. 3005-3010.

Hu, Xiaotang, et al., "Characterization of a Unique Factor-Independent Variant Derived from Human Factor-Dependent TF-1 Cells: A Transformed Event," Leukemia Research, (1998), 22:817-826.

Jackson, Scott A., et al., "Self-Splicing of a Group I Intron Reveals Partitioning of Native and Misfolded RNA Populations in Yeast," RNA, (2006), 12:2149-2159.

Jakowlew, et al., "Expression of Transforming Growth Factor B Ligand and Receptor Messenger RNAs in Lung Cancer Cell Lines," Cell Growth, Apr. 1995, vol. 6, pp. 465-476.

Khatib, Abdel-Majid, et al., "Proprotein Convertases in Tumor Progression and Malignancy," American Journal of Pathology, Jun. 2002, vol. 160, No. 6, pp. 1921-1934.

Kong, Feng-Ming, et al., "Elevated Plasma Transforming Growth Factor-B1 Levels in Breast Cancer Patients Decrease After Surgical Removal of the Tumor," Annals of Surgery, (1995), vol. 222, No. 2, pp. 155-162.

Kumar, Padma, et al., "TAG Xenograft Vaccine: Xenograft-Expanded Autologous Tumor Vaccine Genetically Modified to Express GM-CSF and Block Production of TGFB2," Bio Processing Journal, Spring 2009, pp. 30-36.

Leuschner, Philipp J.F., et al., "Cleavage of the siRNA Passenger Strand During RISC Assembly in Human Cells," EMBO Reports, (2006), vol. 7, No. 3, pp. 314-320.

Levy, Laurence, et al., "Alterations in Components of the TGF-B Superfamily Signaling Pathways in Human Cancer," Cytokine & Growth Factor Reviews, (2006), 17:41-58.

Li, Ming O., et al., "Transforming Growth Factor-B Regulation of Immune Responses," Annu. Rev. Immunol., (2006), 24:99-146.

Lopez de Cicco, Ricardo, et al., "Human Carcinoma Cell Growth and Invasiveness is Impaired by the Propeptide of the Ubiquitous Proprotein Convertase Furin," Cancer Research, May 15, 2005, 65:(10):4162-4171.

Lu, Jun, et al., "TAP-Independent Presentation of CTL Epitopes by Trojan Antigens," J. Immunol., (2001), 166:7063-7071.

Maples, Phillip B., et al., "TAG Vaccine: Autologous Tumor Vaccine Genetically Modified to Express GM-CSF and Block Production of TGFB2," BioProcessing Journal, Sprin 2009, vol. 8, No. 1, 9 pages.

Matranga, Christian, et al., "Passenger-Strand Cleavage Facilitates Assembly of siRNA into Ago2-Containing RNAi Enzyme Complexes," Cell, Nov. 18, 2005, vol. 123, pp. 607-620.

Mbikay, M., et al., "Comparative Analysis of Expression of the Proprotein Convertases Furin, PACE4, PC1 and PC2 in Human Lung Tumours," British Journal of Cancer, (1997), 75(10), pp. 1509-1514.

McMahon, Stephanie, et al., "Alternative Pathway for the Role of Furin in Rumor Cell Invasion Process Enhanced MMP-2 Levels through Bioactive TGFB," Experimental Cell Research, (2003), 291:326-339.

Montenegro, D.E., et al., "TGFB Inhibits GM-CSF-Induced Phosphorylation of ERK and MEK in Human Myeloid Leukemia Cell Lines via Inhibition of Phosphatidylinositol 3-Kinase (PI3-k)," Cell Proliferation, (2009), 42:1-9.

Naganuma, Hirofumi, et al., "Transforming Growth Factor-B Inhibits Interferon-y Secretion by Lymphokine-Activated Killer Cells Stimulated with Tumor Cells," Neurol. Med. Chir., (1996), 36:789-795.

(56) References Cited

OTHER PUBLICATIONS

Nemunaitis, J., et al., "Phase 1/2 Trial of Autologous Tumor Mixed with an Allogeneic GVAX Vaccine in Advanced-Stage Non-Small-cell Lung Cancer," Cancer Gene Therapy, (2006), 13:555-562.

Nemunaitis, John, "GVAX (GMCSF Gene Modified Tumor Vaccine) in Advanced Stage Non Small Cell Lung Cancer," Journal of Controlled Release, (2003), 91:225-231.

Nemunaitis, J., et al., "A Review of Vaccine Clinical Trials for Non-Small Cell Lung Cancer," Expert Opin. Biol. Ther., (2007), 7(1):89-102.

Nemunaitis, John, et al., "Phase II Study of Belagenpumatucel-L, a Transforming Growth Factor Beta-2 Antisense Gene-Modified Allogeneic Tumor Cell Vaccine in Non—Small-Cell Lung Cancer," Journal of Clinical Oncology, Oct. 10, 2008, vol. 24, No. 29, pp. 4721-4730.

Olivares, Jairo, et al., "Phase I Trial of TGF-B2 Antisense GM-CSF-Gene-Modified Autologous Tumor Cell (TAG) Vaccine," Clinical Cancer Research, (2011), 17:183-192.

Page, Robert E., et al., "Increased Expression of the Pro-Protein Convertase Furin Predicts Decreased Survival in Ovarian Cancer," Cellular Oncology, (2007), 29:289-299.

Pearton, David J., et al., "Proprotein Convertase Expression and Localization in Epidermis: Evidence for Multiple Roles and Substrates," Exp. Dermatol, (2001), 10:193-203.

Penafuerte, Claudia, et al., "Novel TGF-B Antagonist Inhibits Tumor Growth and Antiogenesis by Inducing IL-2 Receptor-Driven STAT1 Activation," The Journal of Immunology, May 6, 2011, 13 pages.

Pesu, Marko, et al., "T Cell-Expressed Proprotein Convertase Furin is Essential for Maintenance of Peripheral Tolerance," Nature, Sep. 11, 2008, 455(7210), pp. 246-250.

Pesu, Marko, et al., "Proprotein Convertase Furin is Preferentially Expressed in T Helper 1 Cells and Regulates Interferon Gamma," Blood, Apr. 20, 2006, 108:983-985.

Polak, ME, et al., "Mechanisms of Local Immunosuppression in Cutaneous Melanoma," British Journal of Cancer, (2007), 96:1879-1887.

Rao, etal., "siRNA vs. shRNA: Similarities and Differences", Advanced Drug Delivery Reviews, 2009, 746-759.

Rao, et al., "siRNA vs. shRNA: Similarities and differences", Advanced Drug Delivery Reviews, 2009, 61:746-759.

Templeton, N.S., "Liposomes for Gene Transfer in Cancer Therapy", Methods in Molecular Biology, 2010, 651:271-278.

\* cited by examiner

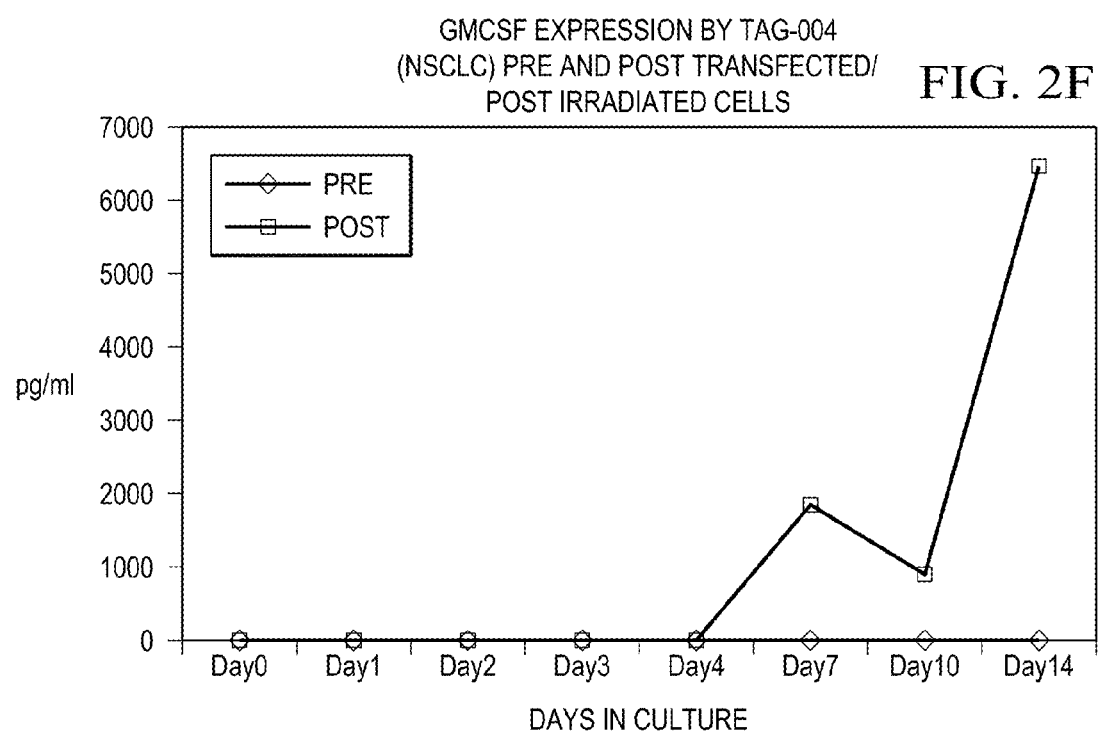

07/07/08
PRE TAG BASELINE

10/05/09
POST TAG

| | TGFβ1 EXPRESSION (Ds",7) | PRE | POST |
|---|---|---|---|
| 1 | LUNG | 5500 | 4600 |
| 2 | LUNG | 6000 | 4900 |
| 3 | LUNG | 5300 | 4900 |
| 4 | LUNG | 4400 | 4900 |
| 5 | LUNG | 5500 | 4400 |
| 6 | LUNG | 180 | 50 |
| 7 | LUNG | 2300 | 1500 |
| 8 | LUNG | 9500 | 7000 |
| 9 | BREAST | 4300 | 4000 |
| 10 | BREAST | 6500 | 6500 |
| 11 | BREAST | 5000 | 4300 |
| 12 | BREAST | 110 | 230 |
| 13 | MELANOMA | 1300 | 1000 |
| 14 | MELANOMA | 5500 | 3700 |
| 15 | MELANOMA | 7100 | 7600 |
| 16 | MELANOMA | 4800 | 4100 |
| 17 | COLON | 4800 | 4500 |
| 18 | COLON | 5100 | 4000 |
| 19 | COLON | 73 | 100 |
| 20 | COLON | 1500 | 1400 |
| 21 | RECTAL | 250 | 600 |
| 22 | OVARIAN | 6500 | 6500 |
| 23 | BLADDER | 357 | 308 |
| 24 | BLADDER | 140 | 200 |
| 25 | NEUROENDOCRINE | 6500 | 6800 |
| 26 | ADRENOCORTICAL | 6500 | 6700 |
| 27 | ADRENOCORTICAL | 800 | 540 |
| 28 | GASTRIC | 85 | 200 |
| 29 | HEPATOCELLULAR | 6200 | 6100 |
| 30 | RENAL | 150 | 1400 |
| 31 | URACHAL | 510 | 690 |
| 32 | PROSTATE | 149 | 404 |
| 33 | LEIOMYOSARCOMA | 400 | 140 |
| 34 | HEMANGIOPERICYTOMA | 1100 | 925 |
| ALL TUMOR | AVE. | 3380 | 3094 |
| | STD.DEV | 2843 | 2968 |
| | MEDIAN | 4350 | 3850 |

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

```
<400> SEQUENCE: 1

Arg Xaa Xaa Arg
1

<210> SEQ ID NO 2
<211> LENGTH: 197
<212> TYPE: RNA
<213> ORGANISM: Artificial Sequence
<220> FEATURE:
<223> OTHER INFORMATION: Synthetic

<400> SEQUENCE: 2
ggauccugcu guugacagug agcgcggaga aaggagugaa accuuaguga agccacagau      60
guaagguuuc acuccuuucu ccuugccuac ugccucggag uccugcuguu gacagugagc     120
gcggagaaag auaugaaacc uuaccacaga uguaagguuu accuccuuuc ccuugccua      180 cugccucgga agcuuug                                                    197

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: decanoyl
<220> FEATURE:
<221> NAME/KEY: MISC_FEATURE
<222> LOCATION: (6)..(6)
<223> OTHER INFORMATION: Chloromethylketone

<400> SEQUENCE: 3

Xaa Arg Val Lys Arg Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: di-tert-butyl dicarbonate
<220> FEATURE:
<221> NAME/KEY: MISC_FEATURE
<222> LOCATION: (6)..(6)
<223> OTHER INFORMATION: 7-amino-4-methl-coumarin fluorophore

<400> SEQUENCE: 4

Xaa Arg Val Arg Arg Xaa
1               5

<210> SEQ ID NO 5
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: PYROGLUTAMYL
<220> FEATURE:
<221> NAME/KEY: MISC_FEATURE
<222> LOCATION: (6)..(6)
```

```
<223> OTHER INFORMATION: 7-amino-4-methl-coumarin fluorophore

<400> SEQUENCE: 5

Xaa Arg Thr Leu Arg Xaa
1               5

<210> SEQ ID NO 6
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: lys or arg

<400> SEQUENCE: 6

Arg Xaa Xaa Arg
1
```

FURIN-KNOCKDOWN AND GM-CSF-AUGMENTED (FANG) CANCER VACCINE

CROSS-REFERENCE TO RELATED APPLICATIONS

This application claims priority to U.S. Provisional Application Ser. Nos. 61/289,681, and 61/309,777 filed Dec. 23, 2009, and Mar. 2, 2010 the entire contents of which are incorporated herein by reference.

TECHNICAL FIELD OF THE INVENTION

The present invention relates in general to the field of vaccine development, and more particularly, to the development of compositions and methods for making and using an autologous cancer vaccine genetically modified for Furin knockdown and GM-CSF expression.

STATEMENT OF FEDERALLY FUNDED RESEARCH

None.

REFERENCE TO A SEQUENCE LISTING

The present application includes a Sequence Listing filed separately in an electronic format as required by 37 C.F.R §1.821-1.825.

BACKGROUND OF THE INVENTION

Without limiting the scope of the invention, its background is described in connection with the development of genetically modified whole cell cancer vaccines. More specifically, the present invention relates to vaccines capable of augmenting tumor antigen expression, presentation, and processing through expression of the GM-CSF transgene and attenuating secretory immunosuppressive activity of TGF-β via furin bi-functional shRNA transgene induced knockdown.

The prevailing hypothesis for immune tolerance to cancer vaccines include the low immunogenicy of the tumor cells, the lack of appropriate presentation by professional antigen presenting cells, immune selection of antigen-loss variants, tumor induced immunosuppression, and tumor induced privileged site. Whole cancer cell vaccines can potentially solicit broad-based, polyvalent immune responses to both defined and undefined tumor antigens, thereby addressing the possibility of tumor resistance through downregulation and/or selection for antigen-loss variants. A method for making a master cell bank of whole cell vaccines for the treatment of cancer can be found in U.S. Pat. No. 7,763,461 issued to Link et al. (2010). According to the '461 patent tumor cells are engineered to express an α (1,3) galactosyl epitope through ex-vivo gene therapy protocols. The cells are then irradiated or otherwise killed and administered to a patient. The α galactosyl epitope causes opsonization of the tumor cell enhancing uptake of the opsonized tumor cell by antigen presenting cells which results in enhanced tumor specific antigen presentation. The animal's immune system thus is stimulated to produce tumor specific cytotoxic cells and antibodies which will attack and kill tumor cells present in the animal Granulocyte-macrophage colony-stimulating factor, often abbreviated to GM-CSF, is a protein secreted by macrophages, T cells, mast cells, endothelial cells and fibroblasts. When integrated as a cytokine transgene, GM-CSF enhances presentation of cancer vaccine peptides, tumor cell lysates, or whole tumor cells from either autologous patient tumor cells or established allogeneic tumor cell lines. GM-CSF induces the differentiation of hematopoietic precursors and attracts them to the site of vaccination. GM-CSF also functions as an adjuvant for dendritic cell maturation and activational processes. However, GM-CSF-mediated immunosensitization can be suppressed by different isoforms of transforming growth factor beta (TGF-β) produced and/or secreted by tumor cells. The TGF-β family of multifunctional proteins possesses well known immunosuppressive activities. The three known TGF-β ligands (TGF-β1, β2, and β3) are ubiquitous in human cancers. TGF-β overexpression correlates with tumor progression and poor prognosis. Elevated TGF-β levels within the tumor microenvironment are linked to an anergic tumor response. TGF-β directly and indirectly inhibits GM-CSF induced maturation of dendritic cells and their expression of MHC class II and co-stimulatory molecules. This negative impact of TGF-β on GM-CSF-mediated immune activation supports the rationale of depleting TGF-β secretion in GM-CSF-based cancer cell vaccines.

All mature isoforms of TGF-β require furin-mediated limited proteolytic cleavage for proper activity. Furin, a calcium-dependent serine endoprotease, is a member of the subtilisin-like proprotein convertase family. Furin is best known for the functional activation of TGF-β with corresponding immunoregulatory ramifications. Apart from the previously described immunosuppressive activities of tumor secreted TGF-β, conditional deletion of endogenously expressed furin in T lymphocytes has been found to allow for normal T-cell development, but impaired function of regulatory and effector T cells, which produced less TGF-β1. Furin expression by T cells appears to be indispensable in maintaining peripheral tolerance, which is due, at least in part, to its non-redundant, essential function in regulating TGF-β1 production.

High levels of furin have been demonstrated in virtually all cancer lines. The inventors and others have found that up to a 10-fold higher level of TGF-β1 may be produced by human colorectal, lung cancer, and melanoma cells, and likely impact the immune tolerance state by a higher magnitude. The presence of furin in tumor cells likely contributes significantly to the maintenance of tumor directed, TGF-β-mediated peripheral immune tolerance. Hence furin knockdown by a RNA interference (RNAi) or other mechanisms represents a novel and attractive approach for optimizing GM-CSF-mediated immunosensitization and vaccine development. Chen et al. (2004) in U.S. Patent Application No. 20040242518 provide methods and compositions for inhibiting influenza infection and/or replication based on the phenomenon of RNAi as well as systems for identifying effective siRNAs and shRNAs for inhibiting influenza virus and systems for studying influenza virus infective mechanisms. The invention also provides methods and compositions for inhibiting infection, pathogenicity and/or replication of other infectious agents, particularly those that infect cells that are directly accessible from outside the body, e.g., skin cells or mucosal cells. In addition, the invention provides compositions comprising an RNAi-inducing entity, e.g., an siRNA, shRNA, or RNAi-inducing vector targeted to an influenza virus transcript and any of a variety of delivery agents. The invention further includes methods of use of the compositions for treatment of influenza Interferon-gamma (γIFN) is a key immunoregulatory cytokine that plays a critical role in the host innate and adaptive immune response and in tumor control. Also known as type II interferon, γIFN is a single-copy gene whose expression is regulated at multiple levels. γIFN coordinates a diverse array of cellular programs through transcriptional regulation of immunologically relevant genes. Initially, it was believed that CD4+ T helper cell type 1 (Th1) lymphocytes, CD8+ cytotoxic lymphocytes, and NK cells exclusively produced γIFN. However, there is now evidence that other cells, such as B cells, NKT cells, and professional antigen-presenting cells (APCs) secrete γIFN. γIFN production by professional APCs [monocyte/macrophage, dendritic cells (DCs)] acting locally may be important in cell self-activation and activation of nearby cells. γIFN secretion by NK cells and possibly professional APCs is likely to be important in early host defense against infection, whereas T lymphocytes become the major source of γIFN in the adaptive immune response. Furthermore, a role for γIFN in preventing development of primary and transplanted tumors has been identified. γIFN production is controlled by cytokines secreted by APCs, most notably interleukin (IL)-12 and IL-18. Negative regulators of γIFN production include IL-4, IL-10, glucocorticoids, and TGF-β.

SUMMARY OF THE INVENTION

The present invention also provides an autologous (i.e., patient specific) cancer vaccine composition (FANG vaccine), comprising a therapeutically effective amount of cells with an shRNAfurin/GM-CSF expression vector. This vector comprises a first nucleic acid encoding GM-CSF, which may be human GM-CSF, and a second nucleic acid insert encoding one or more short hairpin RNAs (shRNA) capable of hybridizing to a region of an mRNA transcript encoding furin, thereby inhibiting furin expression via RNA interference. Both nucleic acid inserts are operably linked to a promoter. The shRNA may be bi-functional, incorporating both (cleavage dependent) RISC (RNA induced silencing complex) formatted) siRNA (cleavage dependent) and (cleavage-independent RISC formatted) either miRNA or miRNA-like motifs simultaneously. In one embodiment of the present invention, the shRNA is both the RISC cleavage dependent and RISC cleavage independent inhibitor of furin expression. Furthermore, the expression vector may contain a picornaviral 2A ribosomal skip peptide intercalated between the first and the second nucleic acid inserts, and the promoter may be CMV mammalian promoter which could contain an enhancer sequence and intron. The mRNA sequences targeted by the bi-functional shRNA are not limited to coding sequences; in one embodiment, the shRNA may target the 3' untranslated region (3'-UTR) sequence of the furin mRNA transcript, and in one embodiment may target both the coding sequence and the 3' UTR sequence of the furin mRNA transcript simultaneously. The cells used to produce the vaccine may be autologous tumor cells, but xenograft expanded autologous tumor cells, allogeneic tumor cells, xenograft expanded allogeneic tumor cells, or combinations of them may also be used. The vaccine dosage administered to patients contains $1 \times 10^7$ cells to $2.5 \times 10^7$ cells. The FANG vaccine can be given in conjunction with a therapeutically effective amount of γIFN (gamma interferon). The dosage range of γIFN may be 50 or 100 µg/m$^2$.

The present invention describes an autologous cell vaccine composition comprising: a bishRNA$^{furin}$/GMCSF expression vector plasmid and one or more optional vaccine. The vector plasmid comprises a first nucleic acid insert operably linked to a promoter, wherein the first insert encodes a Granulocyte Macrophage Colony Stimulating Factor (GM-CSF) cDNA and a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference. In one aspect the GM-CSF is human. In another aspect the shRNA incorporates siRNA (cleavage dependent RISC formatted) and either miRNA or miRNA-like (cleavage-independent RISC formatted) motifs. The shRNA as described herein is both the cleavage dependent RISC formatted and cleavage independent RISC formatted inhibitor of furin expression and is further defined as a bi-functional shRNA.

In another aspect, a picornaviral 2A ribosomal skip peptide is intercalated between the first and the second nucleic acid inserts. In yet another aspect the promoter is a CMV mammalian promoter containing a CMV IE 5' UTR enhancer sequence and a CMV IE Intron A. In a related aspect the CMV mammalian promoter. In other aspects the region targeted by the shRNA is the 3' UTR region sequence of the furin mRNA transcript and the region targeted by the shRNA is the coding region of the furin mRNA transcript.

The present invention provides a method of preventing, treating and/or ameliorating symptoms of a cancer in a patient by comprising the steps of: identifying the patient in need of prevention, treatment, and/or amelioration of the symptoms of the cancer and administering an autologous cell vaccine comprising a bishRNA$^{furin}$/GMCSF expression vector plasmid, wherein the vector plasmid comprises a first nucleic acid insert operably linked to a promoter, wherein the first insert encodes a Granulocyte Macrophage Colony Stimulating Factor (GM-CSF) cDNA, a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference, and one or more optional vaccine adjuvants.

The method further comprises the steps of monitoring the progression of the therapy by measuring a level of a transforming growth factor beta (TGF-beta or TGF-β) and the GM-CSF in the one or more cancer cells, wherein a reduction in the level of TGF-β and an elevation in the level of the GM-CSF is indicative of a successful therapy and altering the administration of the autologous cell vaccine based on the levels of the TGF-β and the GM-CSF. As per the method of the present invention the TGF-β is selected from at least one of TGF-β1, TGF-β2, or TGF-β3. In one aspect the cancer is selected from the group consisting of melanoma, non-small-cell lung cancer, gall bladder cancer, colorectal cancer, breast cancer, ovarian, liver cancer, liver cancer metastases, and Ewing's sarcoma as well as other patient derived TGF-β producing cancers. In another aspect the shRNA incorporates siRNA (cleavage dependent RISC formatted) and either miRNA or miRNA-like (cleavage-independent RISC formatted) motifs and the shRNA is both the cleavage dependent RISC formatted and cleavage independent RISC formatted inhibitor of furin expression. In yet another aspect the shRNA is further defined as a bi-functional shRNA.

In another embodiment the present invention discloses an autologous furin-knockdown and Granulocyte Macrophage Colony Stimulating Factor (GM-CSF) augmented (FANG) cancer vaccine composition comprising: a bishRNA$^{furin}$/GMCSF expression vector plasmid, wherein the vector plasmid comprises a first nucleic acid insert operably linked to a promoter, wherein the first insert encodes the GM-CSF cDNA and a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference and one or more optional vaccine adjuvants. The composition of the present invention is used to prevent, treat, and/or ameliorate the symptoms of a cancer, wherein the cancer is selected from the group consisting of melanoma, non-small-cell lung cancer, gall bladder cancer, colorectal cancer, breast cancer, ovarian, liver cancer, liver cancer metastases, and Ewing's sarcoma as well as other patient derived TGF-β producing cancers.

In yet another embodiment the present invention is a method of treating, preventing, and/or ameliorating the symptoms of a non small cell lung cancer (NSCLC) in a patient by an administration of a furin-knockdown and Granulocyte Macrophage Colony Stimulating Factor (GM-CSF) augmented (FANG) cancer vaccine comprising the steps of: identifying the patient in need of prevention, treatment, and/or amelioration of the symptoms of the NSCLC and administering the FANG vaccine comprising a bishRNA$^{furin}$/GMCSF expression vector plasmid, wherein the vector plasmid comprises a first nucleic acid insert operably linked to a promoter, wherein the first insert encodes the GM-CSF cDNA, a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference, and one or more optional vaccine adjuvants. The method of the instant invention further comprising the steps of: monitoring the progression of the therapy by measuring a level of a transforming growth factor beta (TGF-beta or TGF-β) and the GM-CSF in the one or more NSCLC cells, wherein a reduction in the level of TGF-β and an elevation in the level of the GM-CSF is indicative of a successful therapy and altering the administration of the autologous cell vaccine based on the levels of the TGF-β and the GM-CSF. In one aspect of the present invention the TGF-β is selected from at least one of TGF-β1, TGF-β2, or TGF-β3.

The present invention in a further embodiment describes a method of making a furin-knockdown and Granulocyte Macrophage Colony Stimulating Factor (GM-CSF) augmented (FANG) cancer vaccine comprising the steps of: (i) harvesting one or more cancer cells from a patient aseptically, (ii) placing the harvested cells in an antibiotic solution in a sterile container, (iii) forming a cell suspension from the harvested solution, wherein the formation of the cell, (iv) suspension is achieved by enzymatic dissection, mechanical disaggregation or both, (v) modifying the cells genetically by electroporating the cell suspension to make the vaccine with a bishRNA$^{furin}$/GMCSF expression vector plasmid, wherein the vector plasmid comprises a first nucleic acid insert operably linked to a promoter, wherein the first insert encodes the GM-CSF cDNA, a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference, (vi) harvesting the vaccine, (vii) irradiating the vaccine and (viii) freezing the vaccine.

In one aspect of the method the one or more cancer cells are harvested from a patient suffering from a cancer selected from the group consisting of melanoma, non-small-cell lung cancer, gall bladder cancer, colorectal cancer, breast cancer, ovarian, liver cancer, liver cancer metastases, and Ewing's sarcoma as well as other patient derived TGF-β producing cancers. In another aspect the genetically modified cells have been rendered proliferation-incompetent by irradiation. In yet another aspect the genetically modified cells are autologous, allogenic, or xenograft expanded cells.

In one aspect the allogenic cells are established cell lines. In another aspect the genetically modified cells are administered to the subject once a month for up 12 doses, wherein the dose of genetically modified cells administered to the subject is $1 \times 10^7$ cells/injection to $5 \times 10^7$ cell/injection and the administration of the genetically modified cells is part of a combination therapy with an additional therapeutic agent. In yet another aspect the additional therapeutic agent used in the combination therapy is γIFN, wherein the dose of γIFN administered to the subject in the combination therapy is 50 or 100 µg/m². The method of the present invention further comprises the step of incubating the genetically modified cells with γIFN after transfection, wherein the dose of γIFN applied to the genetically modified cells after transfection is approximately 250 U/ml (500 U/ml over 24 hours to 100 U/ml over 48 hours).

Another embodiment of the invention is a siRNA-mediated method to inhibit the expression of transforming growth factor beta (TGF-β) via furin knockdown. This method comprises the steps of selecting a target cell and transfecting the target cell with an expression vector comprising a promoter and a nucleic acid insert operably linked to the promoter. The insert encodes one or more short hairpin RNAs (shRNA) capable of hybridizing to a region of an mRNA transcript encoding furin, consequently inhibiting furin expression via RNA interference. The shRNA may be bi-functional, i.e., it may simultaneously incorporate siRNA (cleavage dependent RISC formatted) and either miRNA or miRNA-like (cleavage-independent RISC formatted) motifs, and inhibit furin expression in both a cleavage dependent RISC formatted and cleavage independent RISC formatted manner. Additionally, the expression vector may target the coding region of the furin mRNA transcript, or it may target the 3' UTR region sequence of the furin mRNA transcript, or it may target both the coding sequence and the 3' UTR sequence of the furin mRNA transcript simultaneously.

The present invention also provides a method to augment antigen expression, presentation, and processing, and to attenuate secretory immunosuppressive activity of transforming growth factor beta (TGF-beta or TGF-β) in target cells. This method comprises the steps of selecting a target cell and transfecting the target cell with an expression vector comprising two inserts. The technique used to transfect the target cells may be plasmid vector electroporation. The first nucleic acid insert encodes GM-CSF, whereas the second insert encodes one or more short hairpin RNAs (shRNAs) capable of hybridizing to a region of an mRNA transcript encoding furin, thereby inhibiting furin expression via RNA interference. Both inserts are operably linked to a promoter. The TGF-β isoforms whose activation would be precluded by knocking down furin expression include TGF-β-1, TGF-β-2, and TGF-β-3. Target cells may include autologous or allogeneic cells, which may be established human cell lines.

The present invention also includes a method of preventing, treating and/or ameliorating symptoms of cancer by administering the FANG vaccine to patients. This method comprises the steps of: (i) identifying a subject in need of treatment; (ii) harvesting a cancer tissue sample from the subject; (iii) genetically modifying the cancer cells in the harvested cancer sample; and (iv) administering a therapeutically effective dose of genetically modified cells to the subject. The expression vector used to transfect the cells comprises two nucleic acid inserts. The first nucleic acid insert encodes GM-CSF and it is operably linked to a promoter. The second nucleic acid insert is also operably linked to the promoter, and it encodes one or more short hairpin RNAs (shRNAs) capable of hybridizing to a region of an mRNA transcript encoding furin, thereby inhibiting furin expression via RNA interference. In one embodiment of the present invention, the cancer targeted for treatment is a human melanoma or a non-small-cell lung cancer. To render the genetically modified cells proliferation-incompetent, they may be irradiated. The genetically modified cells in the FANG vaccine may be autologous cells, allogeneic cells, xenograft expanded cells, established human cell lines, or combinations of these cellular types. For vaccination, cells are administered to the subject once a month for up 12 doses, each one containing $1 \times 10^7$ cells to $2.5 \times 10^7$ cells. Dose escalation to $5 \times 10^7$ has been shown to be safe.

The genetically modified cells can be administered as a stand-alone therapy; however, they may also be administered as part of a combination therapy. In this embodiment of the invention, the FANG vaccine may be combined with another therapeutic agent[s], such as, but not limited to, IL-12, IL-15 and/or γIFN. When including γIFN in the treatment with FANG vaccine, the method comprises the further step of incubating the genetically modified cells with approximately 100 U/ml of γIFN for 48 hours or 500 U/ml for 24 hours, respectively, after transfection. For combination therapy, cells are administered to the subject once a month for up to 12 doses, each one containing typically $1 \times 10^7$ cells to $2.5 \times 10^7$ cells (although doses up to $5 \times 10^7$ have been shown to be safe) plus a dose of γIFN of 50 or 100 μg/m². The method further comprises the step of incubating the genetically modified cells with γIFN after transfection, wherein the dose of γIFN applied to the genetically modified cells after transfection is approximately 250 U/ml.

The present invention includes a unique method of inhibiting TGF-β through RNA interference with furin, a proprotein convertase involved critically in the functional processing of all TGF-β isoforms. The FANG vector uniquely incorporates a bi-functional small hairpin construct (shRNAfurin) specific for the knockdown of furin. The bi-functional shRNAfurin of the present invention comprises a two stem-loop structure with a miR-30a backbone. The first stem-loop structure is the siRNA precursor component, while the second stem-loop structure is the miRNA-like precursor component. In this embodiment, the strategy is to use a single targeted site for both cleavage and sequestering mechanisms of RNA interference. In one embodiment, the strategy is to use two different targeted sites, one for the cleavage and one for the sequestering component comprised of, but not limited to, the coding region of the mRNA transcript and the 3' UTR region of the mRNA transcript, respectively. In this embodiment, the bi-functional shRNAfurin is comprised of two stem-loop structures with miR-30a backbone; the first stem-loop structure has complete complementary guiding strand and passenger strand, while the second stem-loop structure has three basepair (bp) mismatches at positions 9 to 11 of the passenger strand. In one embodiment, the bi-functional shRNAfurin is comprised of two stem-loop structures with miR-30a backbone; the first stem-loop structure has complete complementary guiding strand and passenger strand, while the second stem-loop structure has three basepair (bp) mismatches at positions 9 to 11 of the guide strand. In other embodiments, basepair (bp) mismatches will occupy positions preventing Ago 2 mediated cleavage and make it thermodynamically favorable for passenger strand departure. In other embodiments the basepair mismatches will occupy positions of the guide strand. The FANG construct contains GM-CSF and the bi-functional shRNAfurin transcripts under the control of a mammalian promoter (CMV) that drives the entire cassette. This construct is used to generate an autologous (i.e., patient specific) cancer vaccine genetically modified for furin knockdown and GM-CSF expression.

The construct used to produce the FANG vaccine in the present invention includes a bi-functional shRNAfurin/GMCSF expression vector plasmid comprising two nucleic acid inserts. The first nucleic acid insert is linked operably to a promoter, and it encodes a Granulocyte Macrophage Colony Stimulating Factor (GM-CSF) cDNA. The second nucleic acid insert is also linked operably to the promoter, and it encodes one or more short hairpin RNAs (shRNA) capable of hybridizing to a region of an mRNA transcript encoding furin, thereby inhibiting furin expression via RNA interference. The bi-functional shRNA of the present invention has two mechanistic pathways of action, that of the siRNA and that of the miRNA. Thus, the bi-functional shRNA of the present invention is different from a traditional shRNA, i.e., a DNA transcription derived RNA acting by the siRNA mechanism of action or from a "doublet shRNA" that refers to two shRNAs, each acting against the expression of two different genes but in the traditional siRNA mode. In one embodiment of the invention, the GM-CSF is human. The shRNA is bi-functional, incorporating both siRNA (cleavage dependent RISC formatted) and either miRNA or miRNA-like (cleavage-independent RISC formatted) motifs simultaneously. In one embodiment of the present invention, the shRNA is both the cleavage dependent RISC formatted and cleavage independent RISC formatted inhibitor of furin expression. The expression vector may contain a picornaviral 2A ribosomal skip peptide intercalated between the first and the second nucleic acid inserts, and the promoter may be CMV mammalian promoter which could contain a CMV IE 5' UTR enhancer sequence and a CMV IE Intron A. The mRNA sequences targeted by the bi-functional shRNA are not limited to coding sequences; in one embodiment, the shRNA may target the 3' untranslated region (UTR) sequence of the furin mRNA transcript and, in one embodiment, target both the coding sequence and the 3' UTR sequence of the furin mRNA transcript simultaneously The present invention also includes a vector that may be used to specifically knock down the expression of furin in target cells. This shRNAfurin expression vector comprises a nucleic acid insert linked operably to a promoter. Such insert encodes one or more short hairpin RNAs (shRNA) capable of hybridizing to a region of an mRNA transcript encoding furin, thereby inhibiting furin expression via RNA interference. The bi-functional shRNA may simultaneously incorporate siRNA (cleavage dependent RISC formatted) and either miRNA or mi-RNA-like (cleavage-independent RISC formatted) motifs, and inhibit furin expression in both a cleavage dependent RISC formatted and cleavage independent RISC formatted manner. Additionally, the expression vector may target the coding region of the furin mRNA transcript, or it may target the 3' UTR region sequence of the furin mRNA transcript, or it may target both the coding sequence and the 3' UTR sequence of the furin mRNA transcript simultaneously.

BRIEF DESCRIPTION OF THE DRAWINGS

For a more complete understanding of the features and advantages of the present invention, reference is now made to the detailed description of the invention along with the accompanying figures and in which:

FIGS. 2A-2F are plots showing: (2A) TGF-β1, (2B) TGF-β2, and (2C) GMCSF expression in FANG-004 tumor cells pre and post FANG cGMP plasmid transfection and (2D)

Figure 3A:
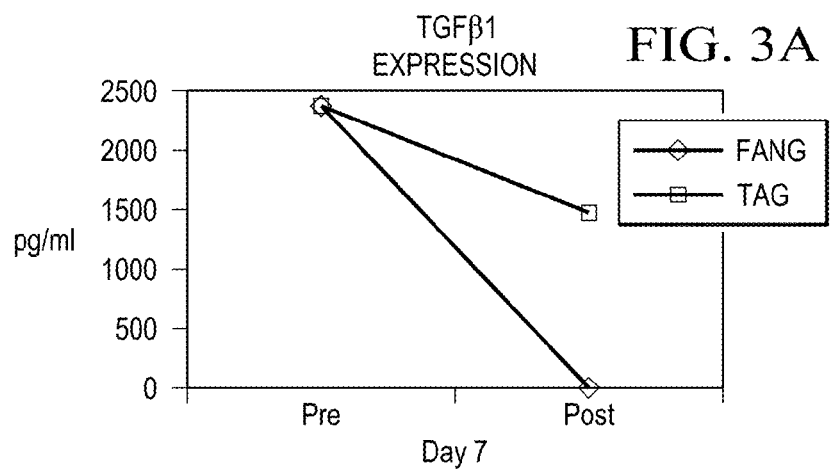
Figure 3B:
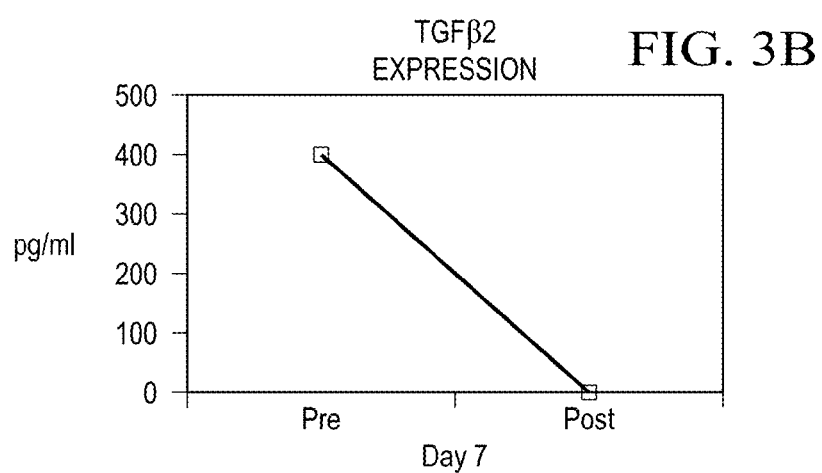
Figure 3C:
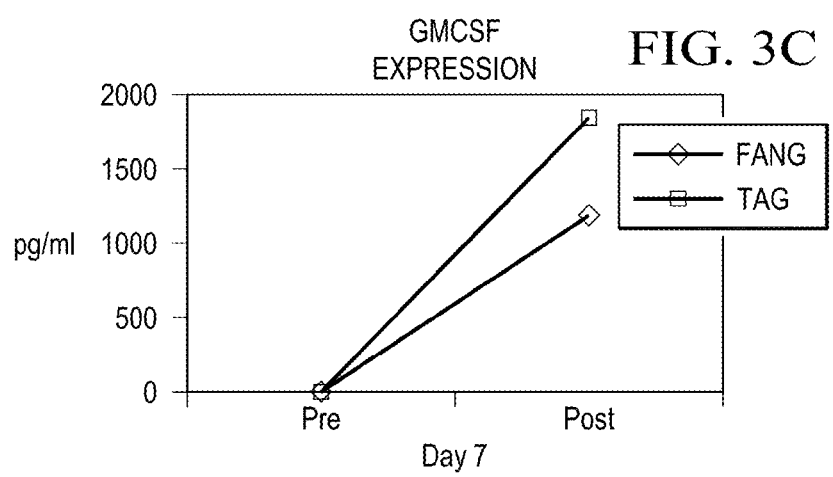
Figure 4A:
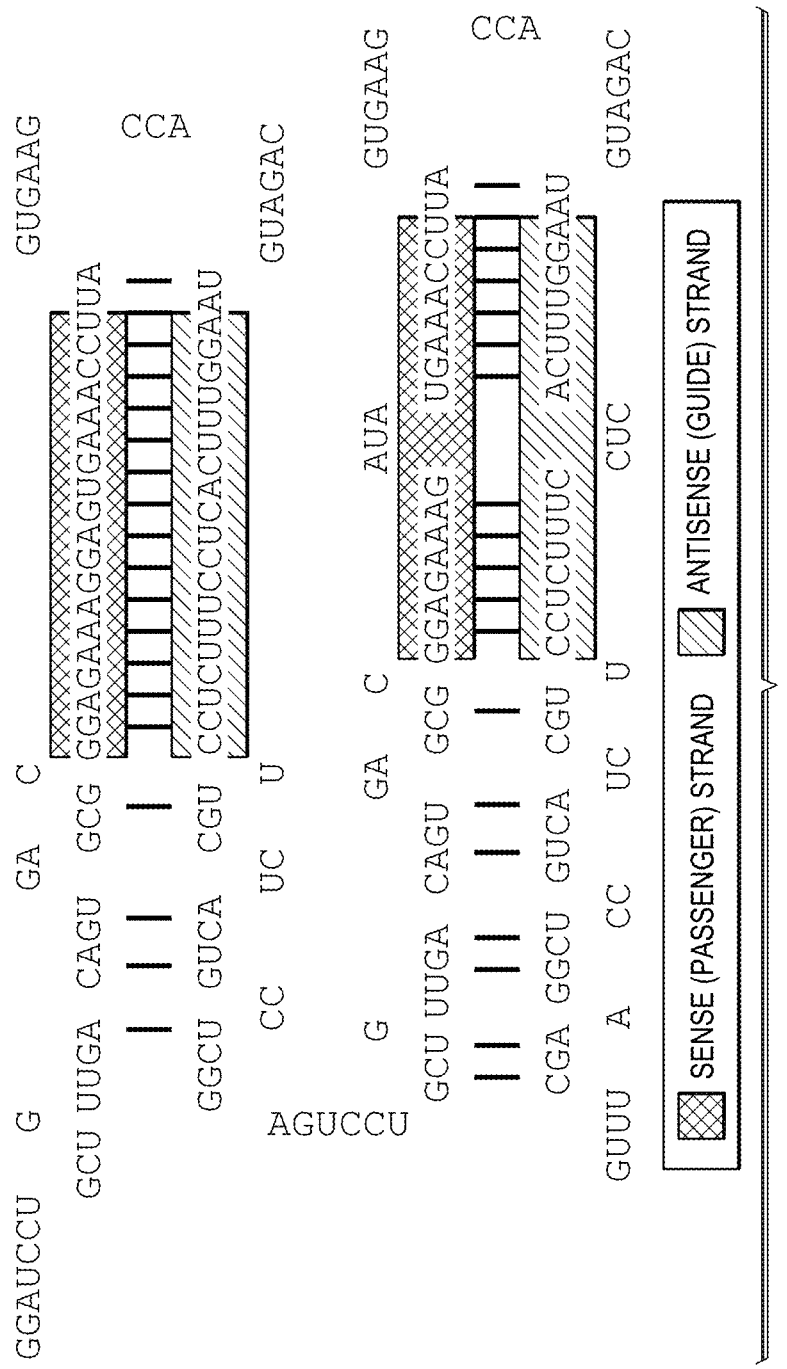
Figure 4B:
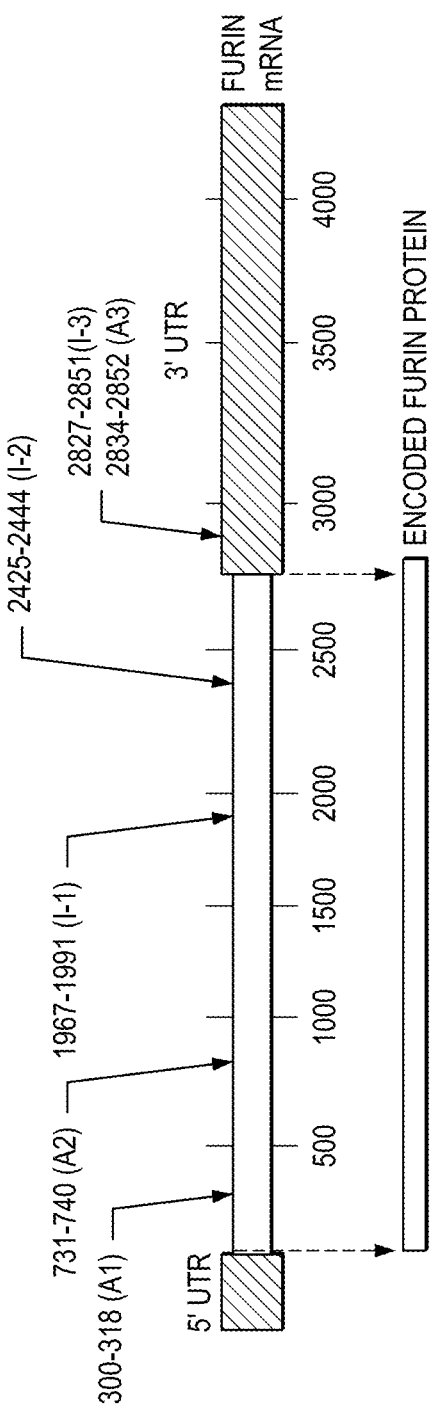
Figure 5:
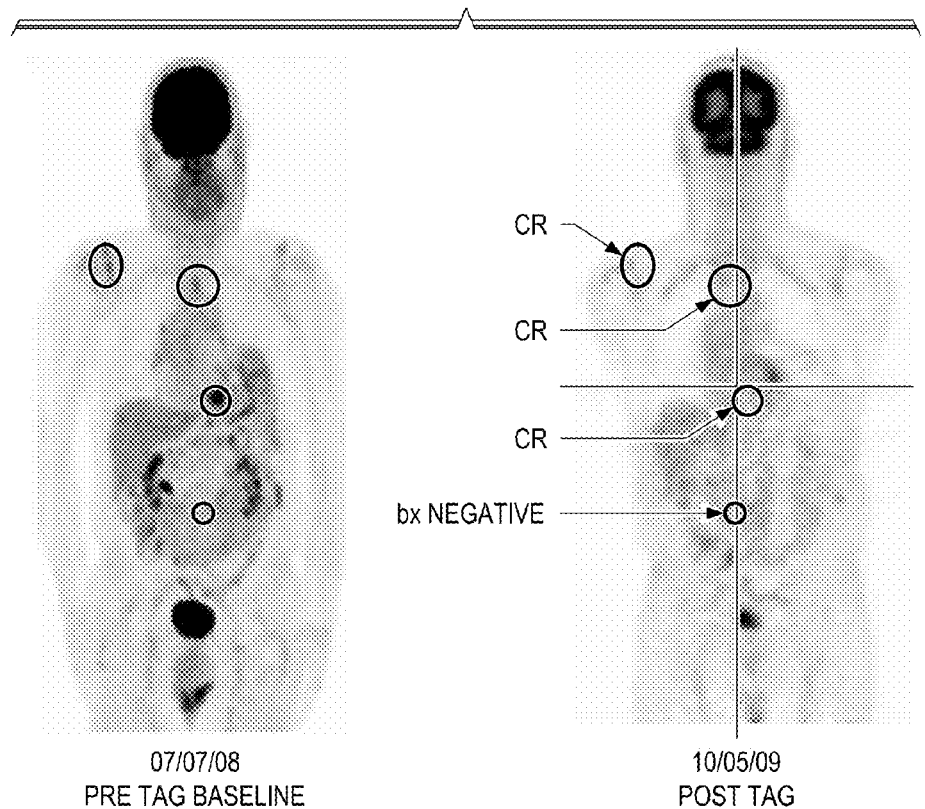
Figure 6A:
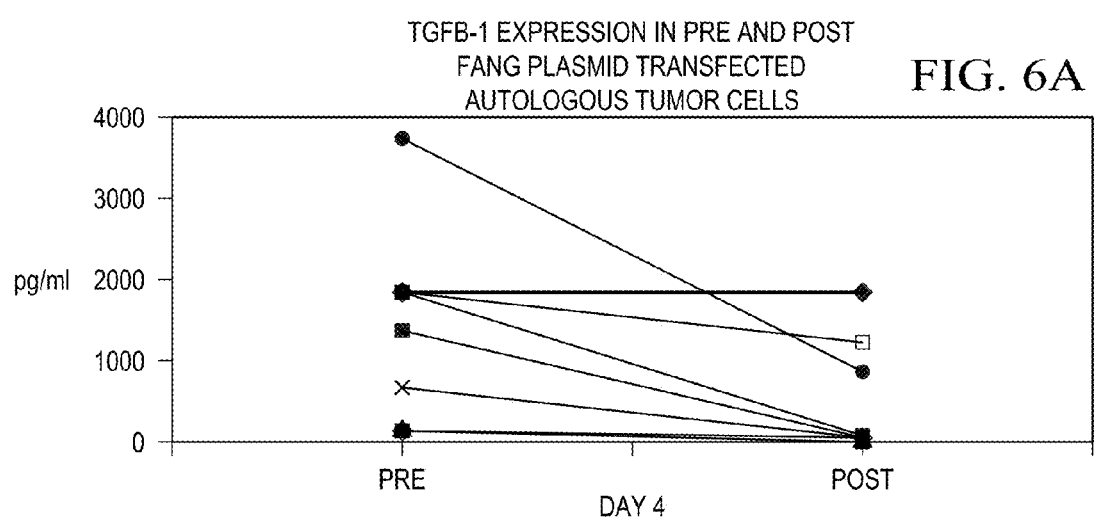
Figure 6B:
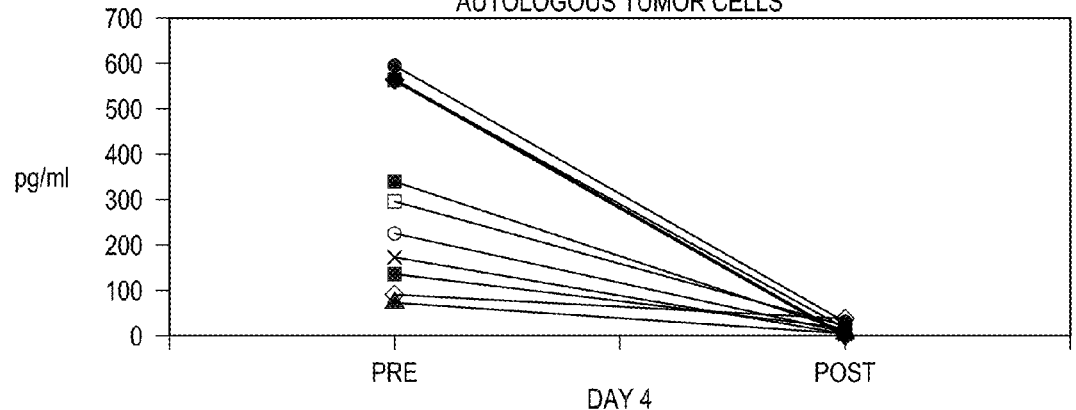
Figure 6C:
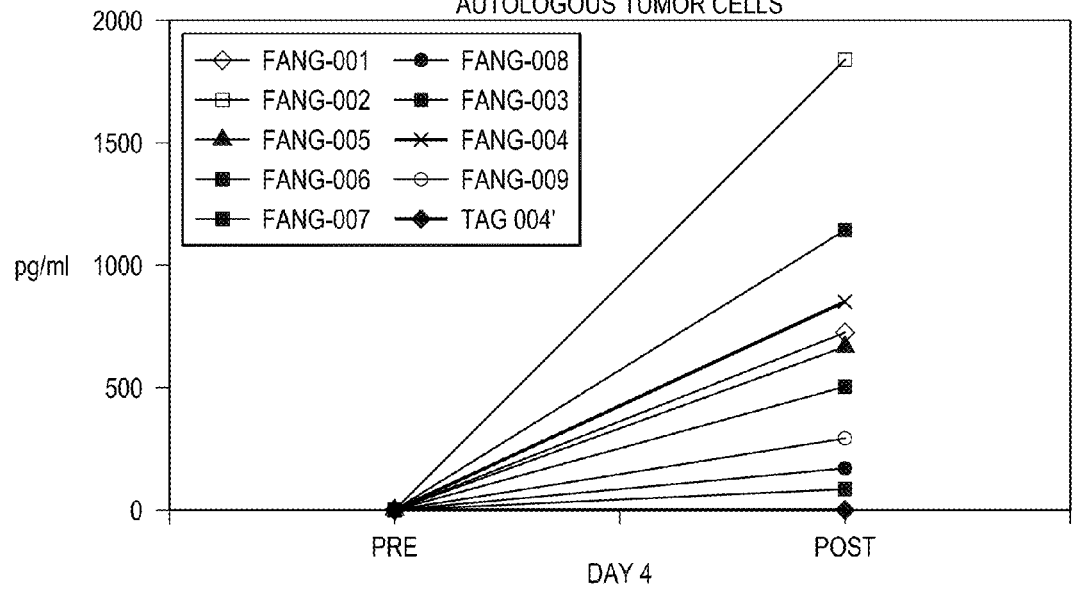
Figure 7:
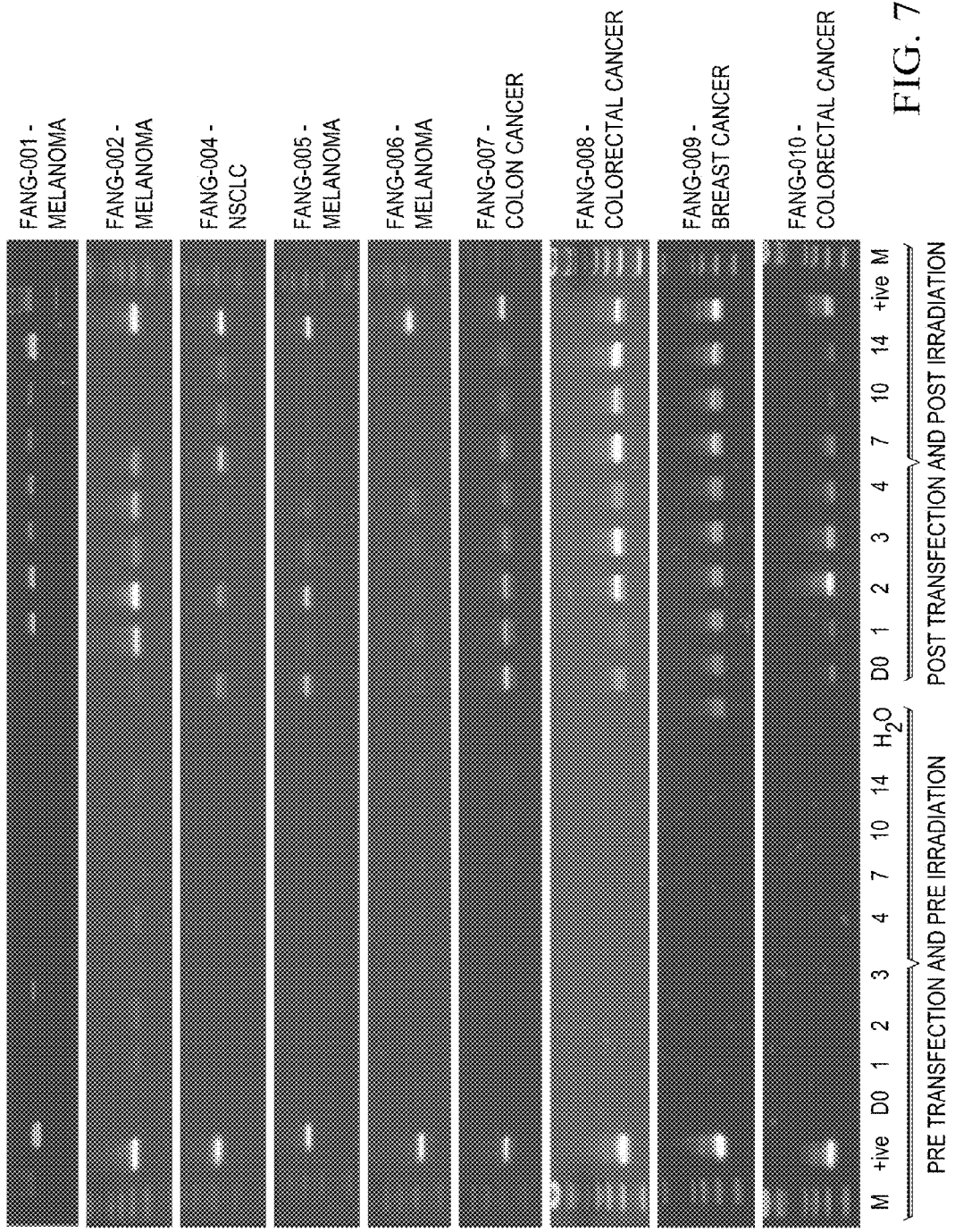
Figure 8:
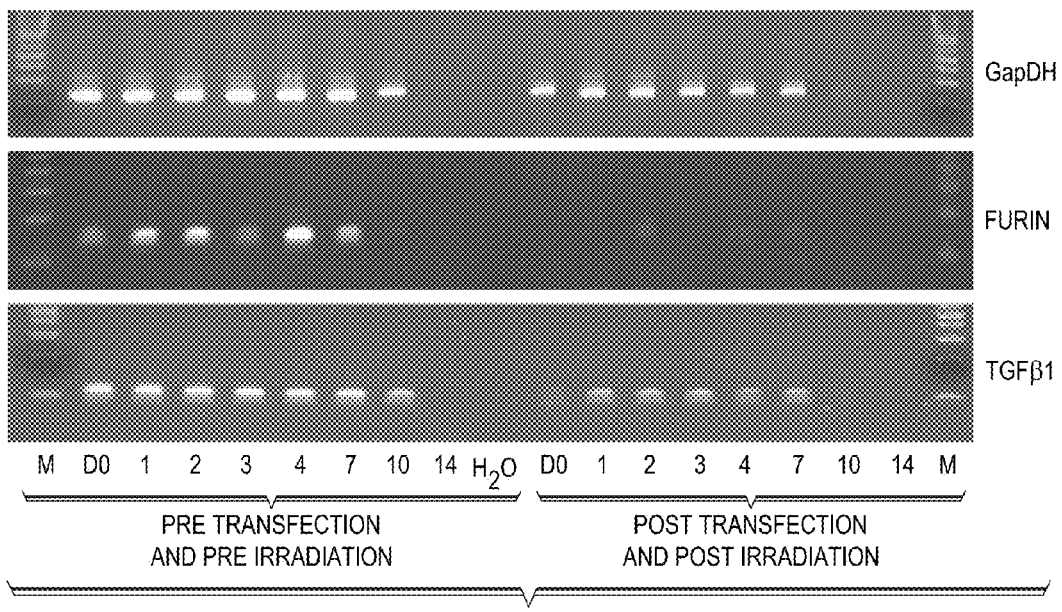
Figure 9:
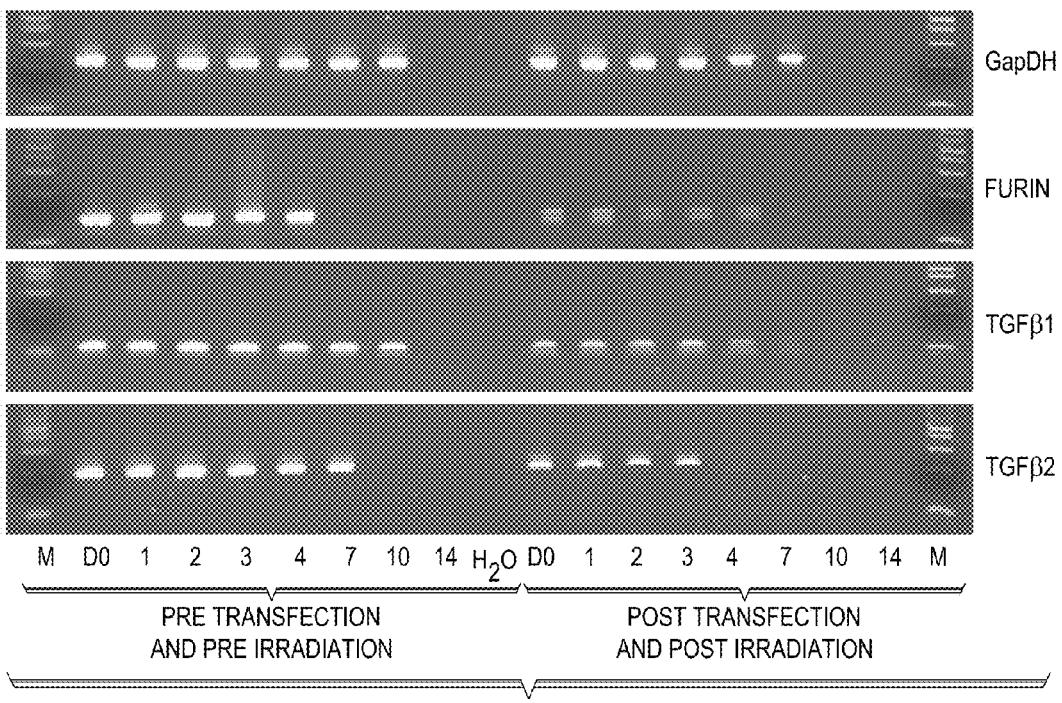
Figure 10:
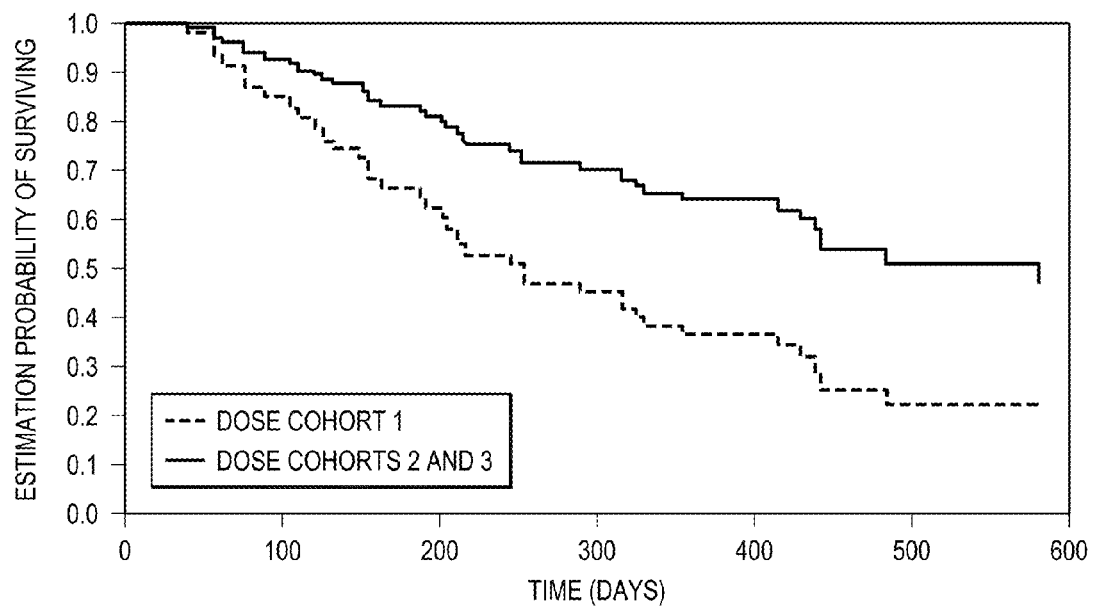
Figure 11:
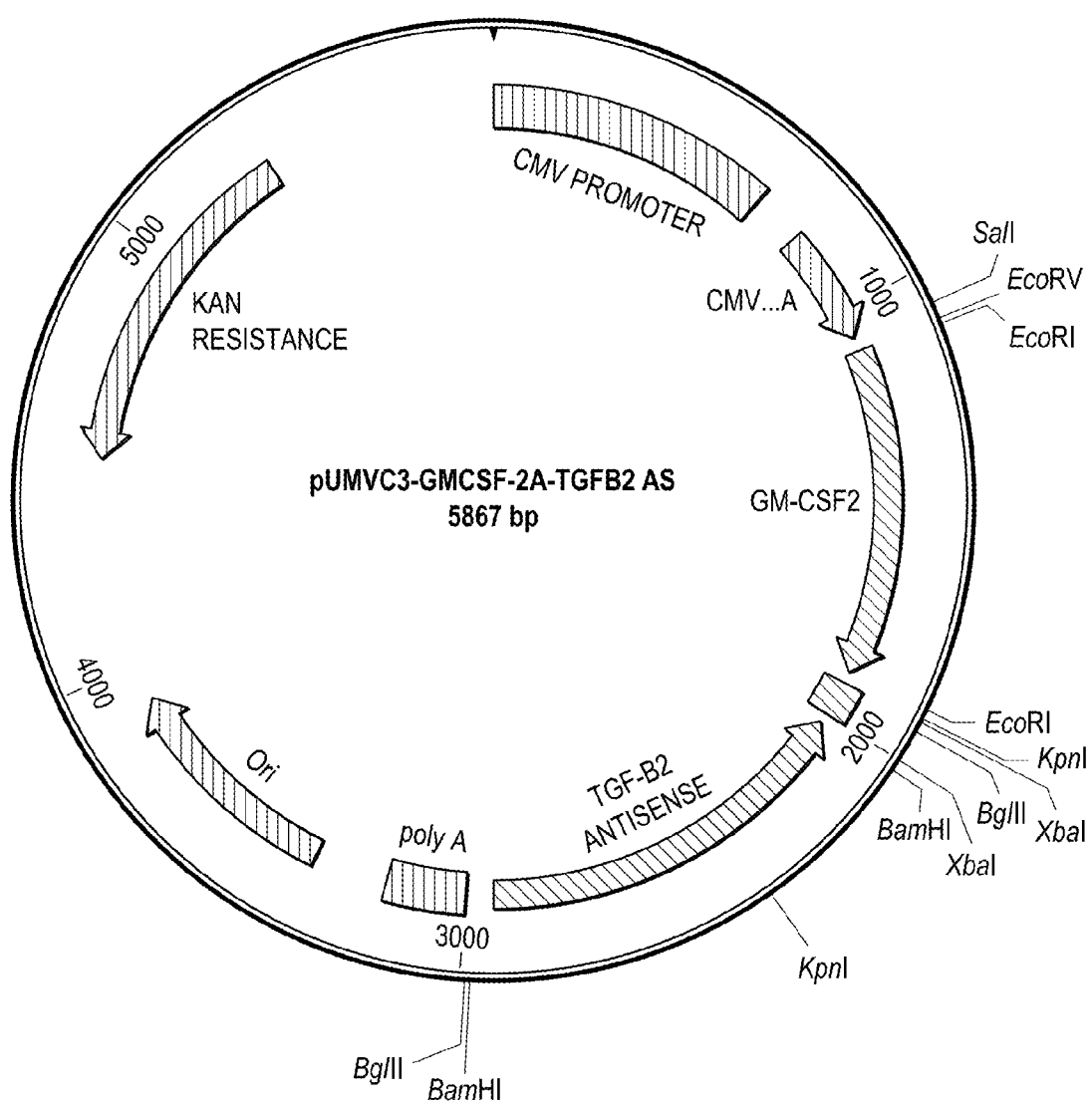
Figure 12:
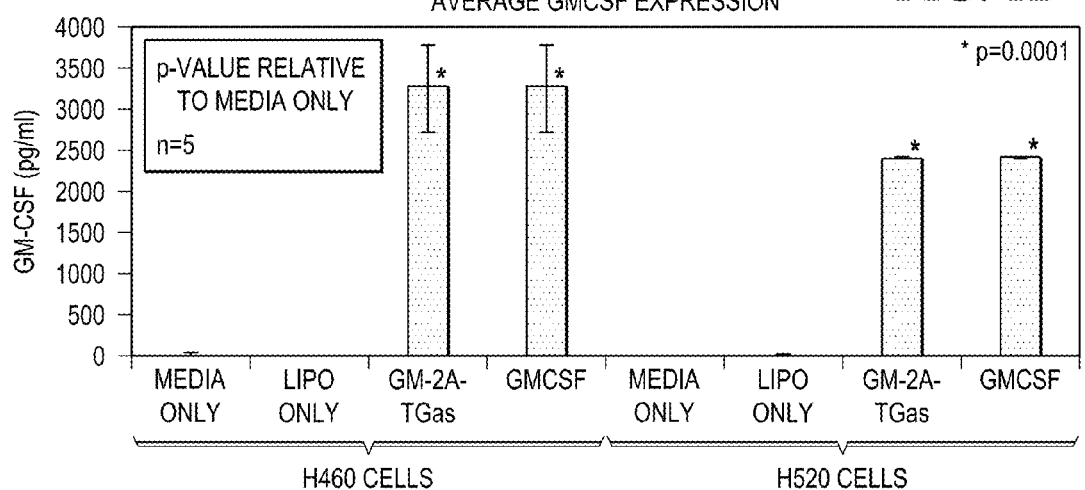
Figure 13:
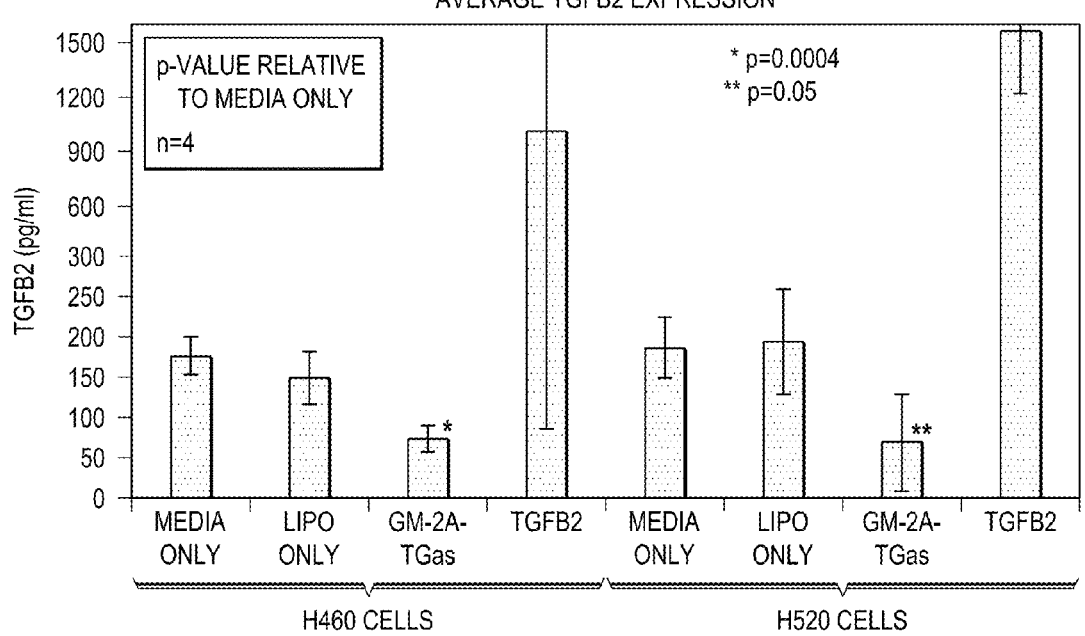
Figure 14:
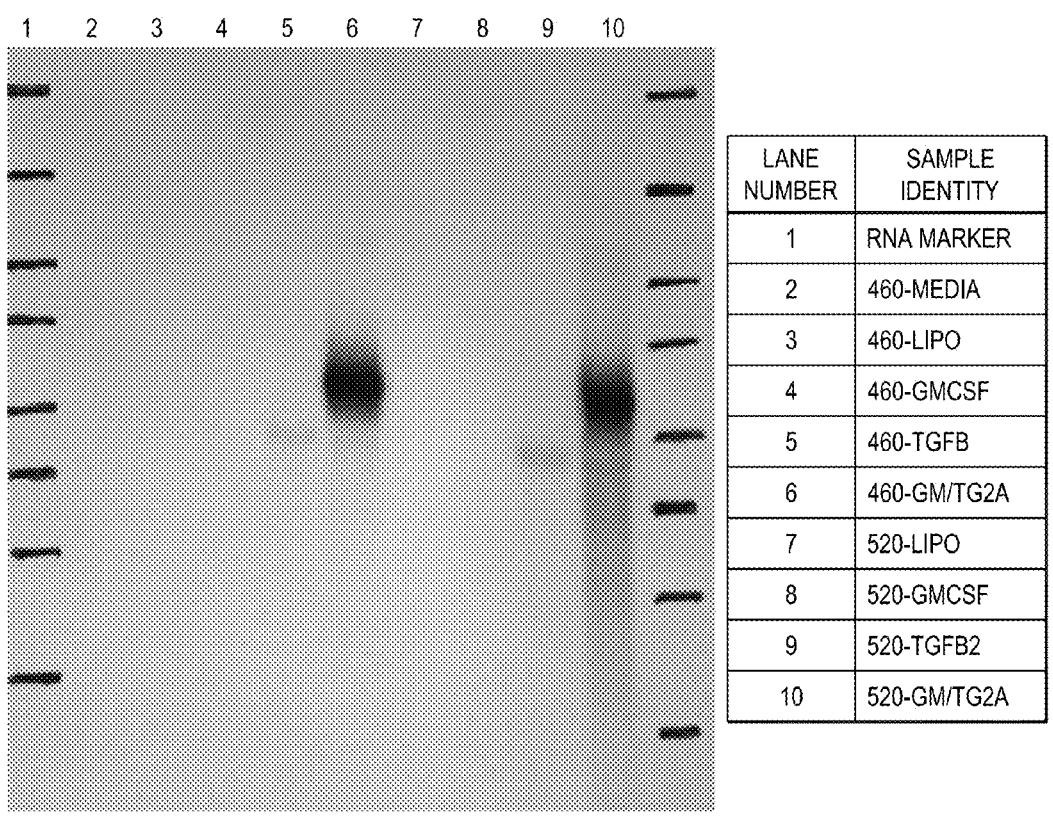
Figure 15:
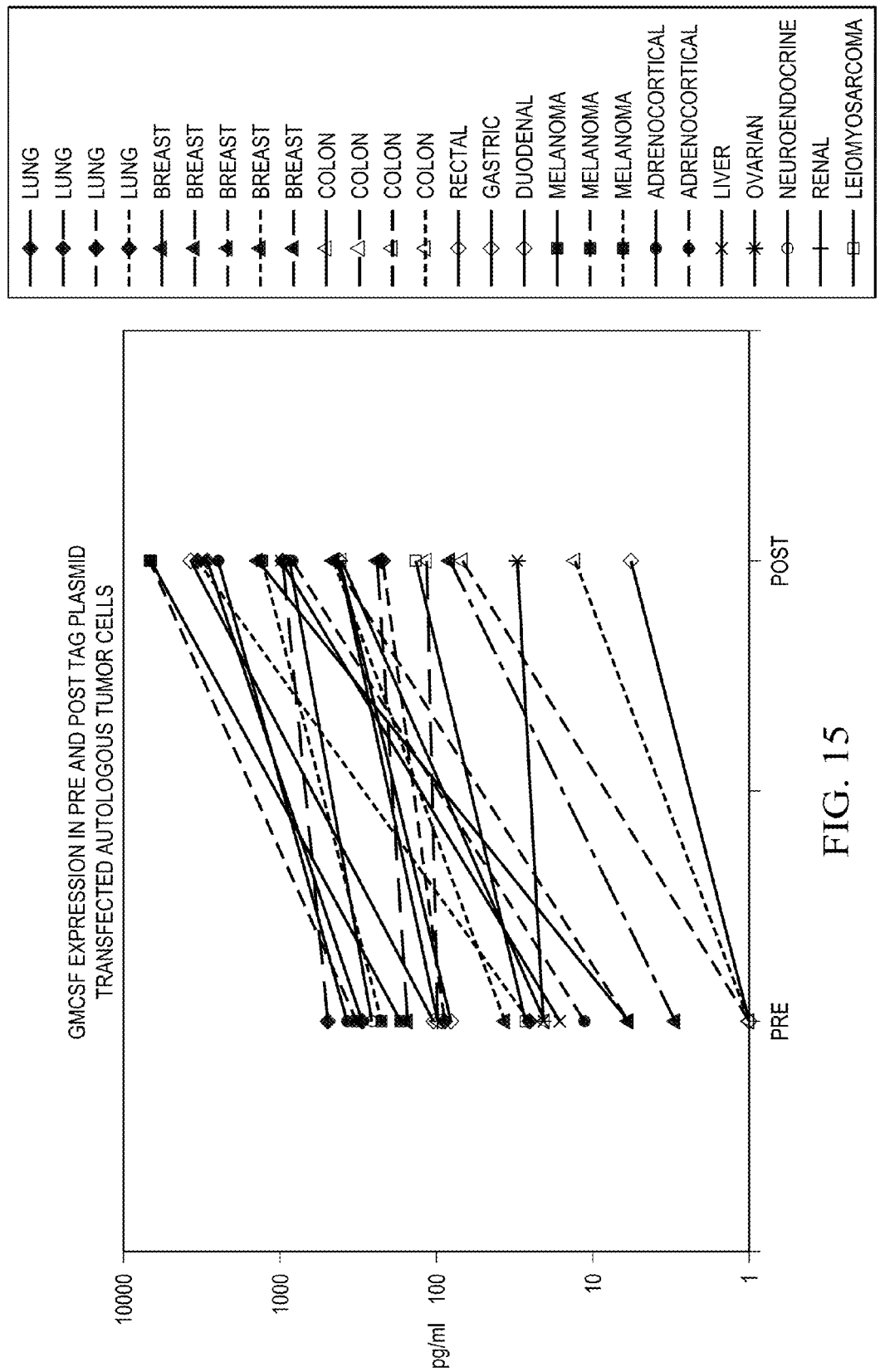
Figure 16:
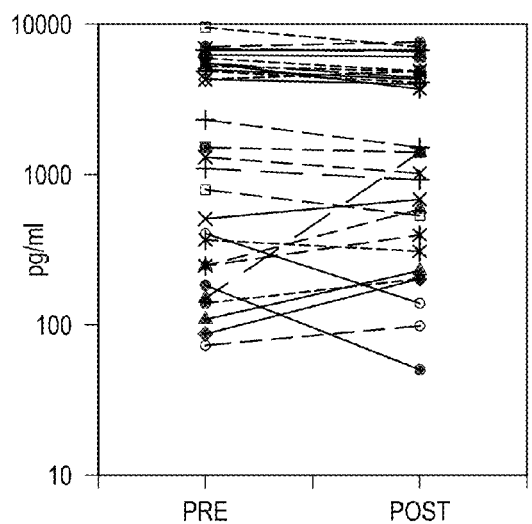

TGF-β1, (2E) TGF-β2, and (2F) GMCSF expression in TAG-004 tumor cells pre and post TAG cGMP plasmid transfection. FANG-004 and TAG-004 are from the same tumor and processed sequentially on the same two days as a demonstration of comparative expression profiles;

FIGS. 3A-3C are plots showing that the side-by-side comparison of electroporation of FANG plasmid (the cGMP vaccine manufacturing process) versus the TAG plasmid into patient tumor cells demonstrated (3C) GMCSF protein production and concomitantly; (3A) TGF-131 expression knocked down by FANG but not TAG and (3B) TGF-β2 knockdown by both FANG and TAG (coincident line);

FIG. 4A is a schematic showing the bi-shRNA$^{furin}$ comprising two stem-loop structures with miR-30a backbone; the first stem-loop structure has complete complementary guiding strand and passenger strand, while the second stem-loop structure has three basepair (bp) mismatches at positions 9 to 11 of the passenger strand. The nucleotide sequence depicted in FIG. 4A is identified by sequence identifier SEQ ID NO: 2;

FIG. 4B shows the siRNA targeted regions of furin mRNA. Prospective siRNA targeting regions in 3'-UTR and encoding regions of furin mRNA and the targeted sequence by each siRNA;

FIG. 5 is an image shows PET CT 11 cycles in a patient after TAG demonstrating significant response. Residual uptake at L 2 was followed up with a MRI scan and biopsy which revealed no malignancy;

FIGS. 6A-6C show an assessment of GMCSF expression and TGF-β1 and -β2 knockdown, summarizing: (6A) TGF-β1, (6B) TGF-β2, and (6C) GM-CSF protein production before and after FANG or TAG (TAG 004) plasmid transfection. Values represent ELISA determinations of cytokine production in harvested autologous cancer cells transfected with FANG. Data represents autologous vaccines independently generated from 9 patients who underwent FANG processing (FANG 001-009). One patient had sufficient tissue to construct both a FANG (blue) and TAG vaccine (red) (FANG 004/TAG 004);

FIG. 7 shows the GMCSF mRNA by RT-qPCR in Pre and Post FANG Transfected/Irradiated Tumor Cells. Absent bands in some of the lanes is due to degraded RNA. (The extra band in FANG-009 is Day 0 sample loaded twice);

FIG. 8 shows FANG Vaccine cells from a patient pre-transfection and post-transfection, irradiation mRNA by PCR. No signal was detected in pre- and post-samples for TGF-β2;

FIG. 9 shows FANG-009 Vaccine cells pre-transfection and post-transfection/irradiation mRNA by PCR;

FIG. 10 shows the overall survival for Cohort 1 versus Cohorts 2 and 3 for advanced-stage patients (n=61; P=0.0186);

FIG. 11 shows a schematic diagram of GM-CSF-TGF-β2 antisense (TAG) plasmid;

FIG. 12 shows the expression of GM-CSF in NCI-H-460 Squamous Cell and NCI-H-520, Large Cell (NSCLC) containing the pUMVC3-GM-CSF-2A-TGF-β2 antisense vector, in vitro;

FIG. 13 shows that TGF-β2 levels are reduced in NCI-H-460 Squamous Cell and NCI-H-520, Large Cell (NSCLC) with the pUMVC3-GM-CSF-2A-TGF-β2 antisense (TAG) vector;

FIG. 14 shows that a 251 base pair probe specifically detects the GM-CSF-2A-TGF-β2 (TAG) transcript expressed in vitro in NCI-H-460 and NCI-H-520 cells (lanes 6 and 10);

FIG. 15 shows the GM-CSF expression in TAG vaccines;

FIG. 16 shows the TGF-β1 expression in TAG vaccines

Figure 17:
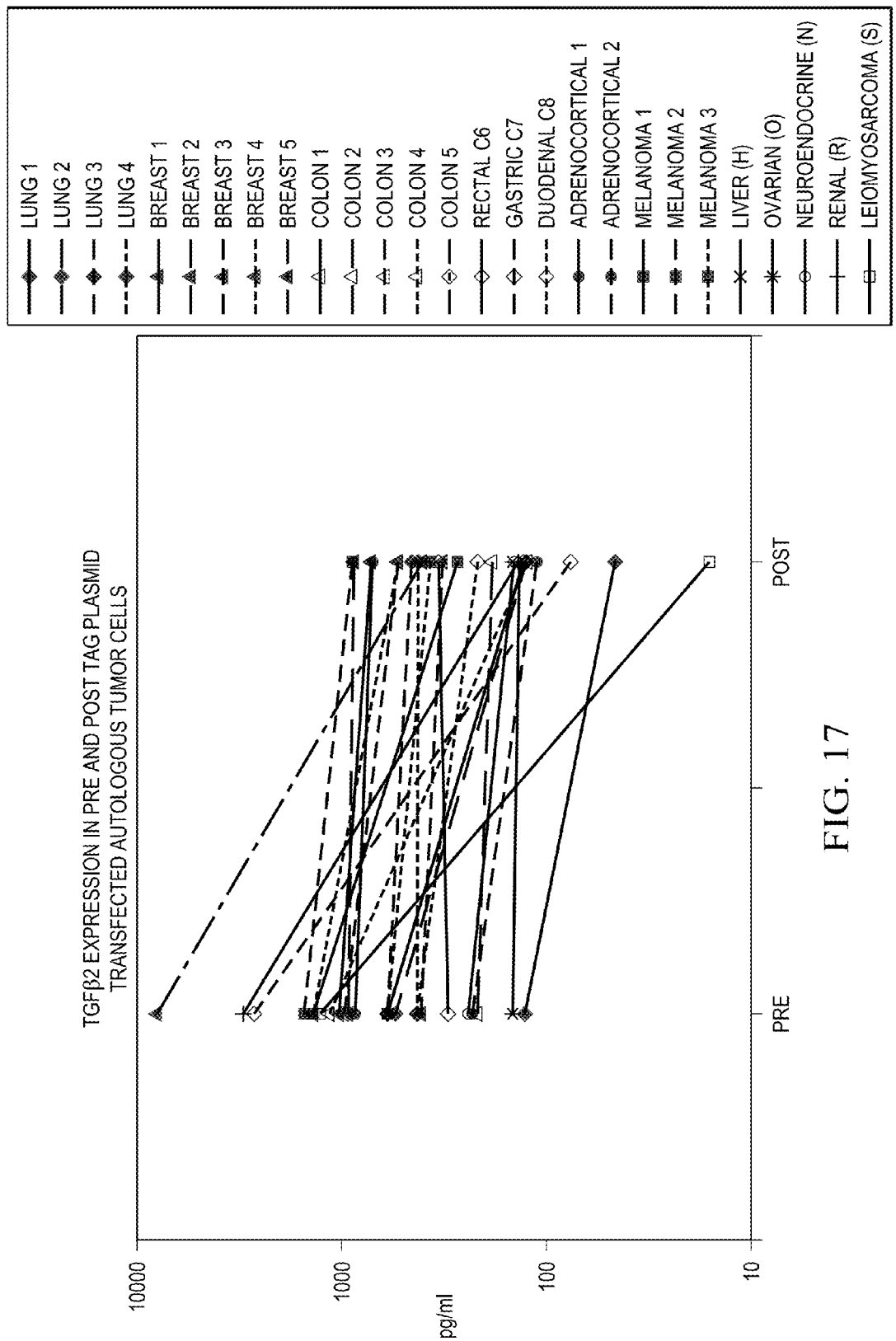
Figure 18A:
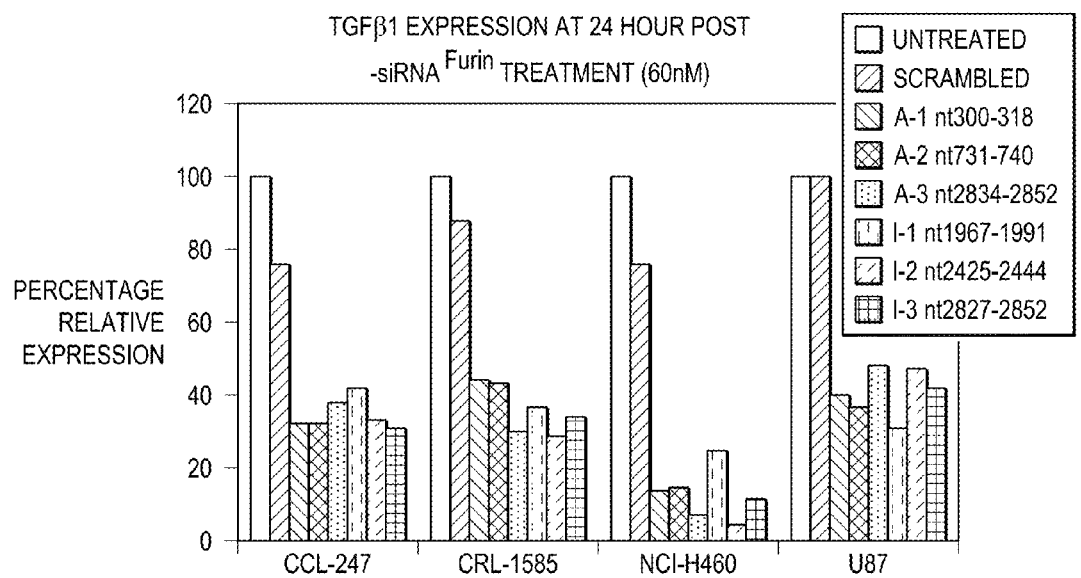
Figure 18B:
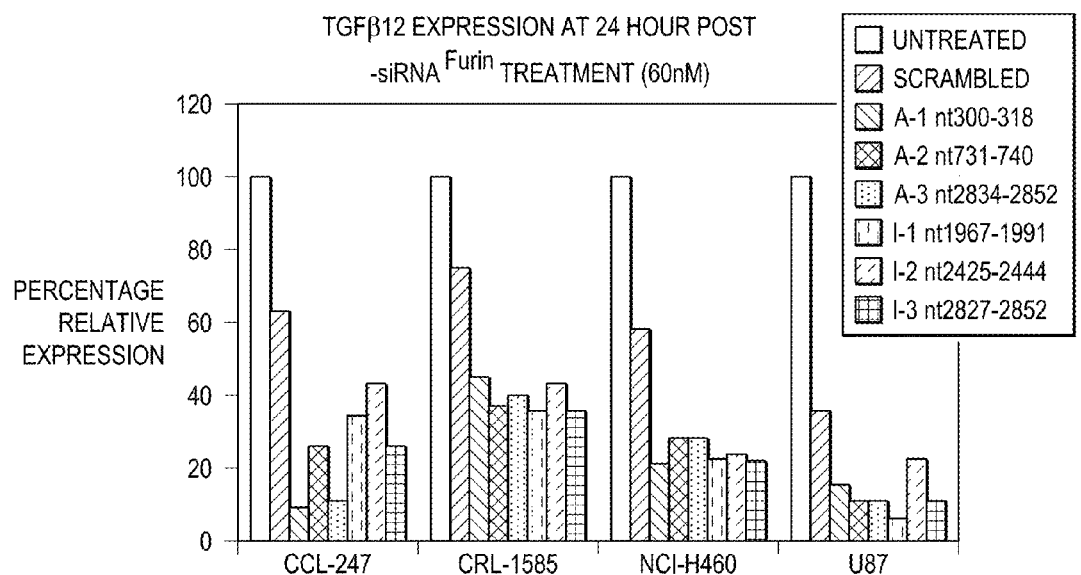
Figure 19:
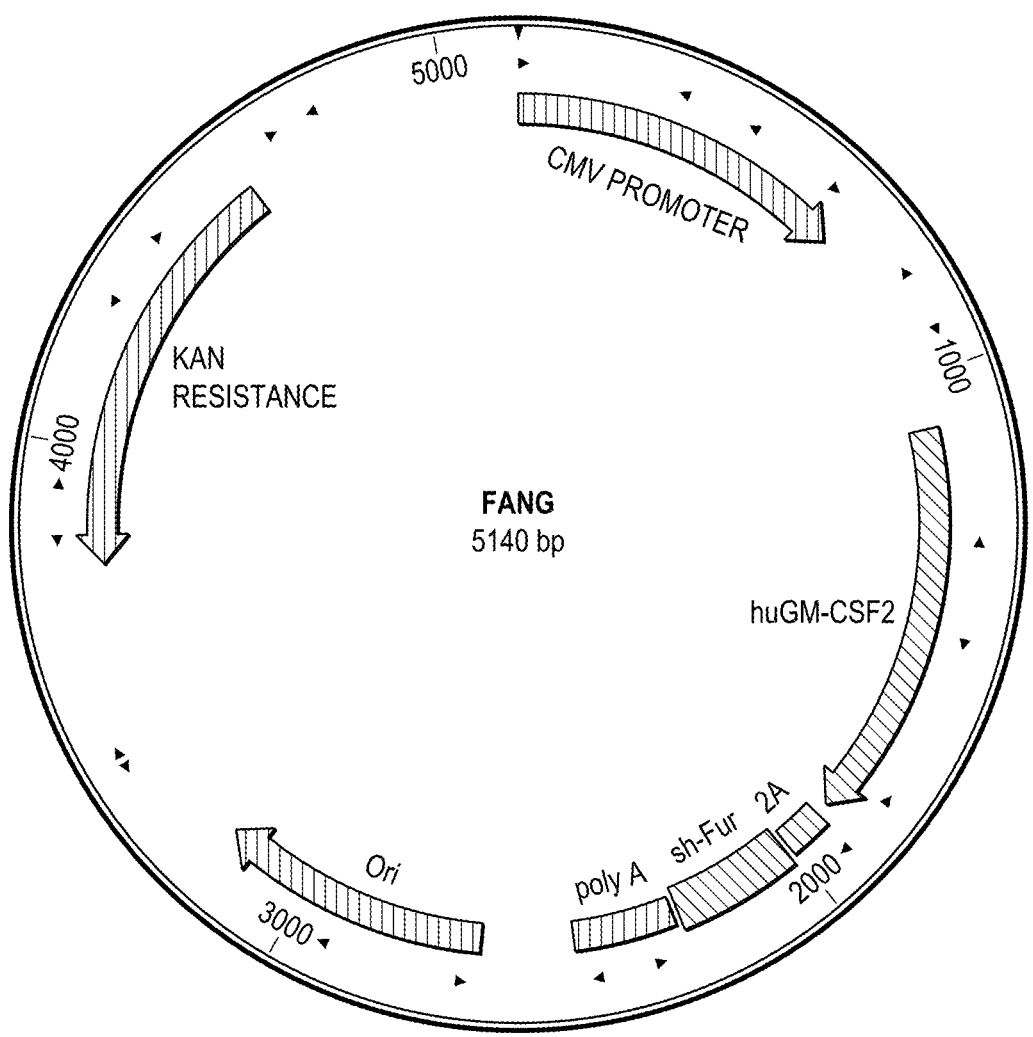

FIG. 17 shows the TGF-β2 expression in TAG vaccines;

FIGS. 18A and 18B show expression of: (14A) TGF-β1 and (14B) TGF-β2 in human cancer lines following siRNA furin knockdown; and FIG. 19 shows the plasmid construct of FANG.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "expression vector" as used herein in the specification and the claims includes nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1)

transcription, 2) translation or 3) mRNA stability, compared to transcription, translation or mRNA stability (longer half-life of mRNA) in the absence of the promoter sequence, under appropriate growth conditions.

The term "oncogene" as used herein refers to genes that permit the formation and survival of malignant neoplastic cells (Bradshaw, T. K.: Mutagenesis 1, 91-97 (1986).

As used herein the term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

The term "hybridizing" refers to any process by which a strand of nucleic acid binds with a complementary strand through base pairing.

The term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

A list of some of the abbreviations used throughout the specification and the claims are listed herein below in Table 1.

TABLE 1

Abbreviations Table

| Abbreviation | Term |
| --- | --- |
| AE | Adverse event |
| ALT | Alanine transaminase (also referred to as SGPT) |
| ANC | Absolute neutrophil count |
| APC | Antigen Presenting Cells |
| AST | Aspartate transaminase (also referred to as SGOT) |
| BUN | Blood urea nitrogen |
| CBC | Complete blood count |
| CD | Cluster of differentiation |
| CMV | Cytomegalovirus |
| $CO_2$ | Total carbon dioxide |
| CR | Complete response |
| CRF | Case report form |
| CTCAE | Common Toxicity Criteria for Adverse Events |
| CTL | Cytotoxic T lymphocyte |
| DC | Dendritic cell(s) |
| DTH | Delayed-type hypersensitivity |
| ECOG PS | Eastern Cooperative Oncology Group Performance Score |
| ELISA | Enzyme-Linked ImmunoSorbent Assay |
| ELISPOT | Enzyme-Linked ImmunoSorbent Spot |
| ER | Endoplasmic reticulum |
| FANG | bishRNA$^{furin}$ and GMCSF Augmented Autologous Tumor Cell Vaccine |

TABLE 1-continued

Abbreviations Table

| Abbreviation | Term |
| --- | --- |
| FL | Flt-3-Ligand |
| GM-CSF | Granulocyte Macrophage-Colony Stimulating Factor Factor (Accession No. NM_000758) |
| GMP | Good manufacturing practice |
| GVAX | GMCSF Secreting autologous or allogenic tumor cells |
| HLA | Human Leukocyte Antigen |
| IBC | Institutional Biosafety Committee |
| IEC | Independent Ethics Committee |
| IL | Infiltrating lymphocytes |
| IRB | Institutional Review Board |
| LAK | Lymphokine-activated killer |
| LD | Longest diameter |
| LLC | Large latent complex |
| MHC | Major histocompatability complex |
| MLR | Mixed lymphocyte reaction |
| MR | Mannose receptor |
| NK | Natural Killer |
| NKT | Natural Killer T cell(s) |
| NSCLC | Non small cell lung cancer |
| PCR | Polymerase chain reaction |
| PD | Progressive disease |
| PR | Partial response |
| PS | Performance Status |
| RECIST | Response Evaluation Criteria in Solid Tumors |
| SCLC | Small cell lung cancer |
| SD | Stable disease |
| SLC | Small latent complex |
| STMN1 | Stathmin 1 |
| TAP | transporter associated with Ag processing |
| TGF-β | Transforming growth factor-β |
| TIL | Tumor infiltrating lymphocytes |
| TNF | Tumor necrosis factor |
| ULN | Upper limits of normal |
| WNL | Within normal limits |

Furin is a member of the subtilisin-like proprotein convertase family. The members of this family are proprotein convertases (PCs) that process latent precursor proteins into their biologically active products. Furin, a calcium-dependent serine endoprotease, efficiently cleaves precursor proteins at their paired basic amino acid processing sites by the consensus sequence -Arg-X-K/Arg-Arg (RXK/RR), with -RXXR- constituting the minimal cleavage site. Like many other proteases, PCs are synthesized as inactive zymogens with an N-terminal prosegment extension, which is autocatalytically removed in the endoplasmic reticulum to achieve functionality.

High levels of furin have been demonstrated in virtually all cancer lines (Furin, Accession No. NM_002569). A 10-fold higher level of TGF-β1 may be produced by human colorectal, lung cancer and melanoma cells, and likely impact the immune tolerance state by a higher magnitude. Transforming growth factors betas (TGF-β) are a family of multifunctional proteins with well known immunosuppressive activities. The three known TGF-β ligands (TGF-β1-3, Accession Nos. NM_000660, NM_003238, NM_003239.2, respectively) are ubiquitous in human cancers. TGF-β overexpression correlates with tumor progression and poor prognosis. Elevated TGF-β levels within the tumor microenvironment are linked to an anergic antitumor response. The presence of furin in tumor cells likely contributes significantly to the maintenance of tumor directed TGF-β1 peripheral immune tolerance. Hence, furin knockdown represents a novel and attractive approach for optimizing immunosensitization.

A Furin-knockdown and GM-CSF-augmented (FANG) Autologous Cancer Vaccine for Human Melanoma and Lung Cancer: FANG uniquely incorporates a bi-functional small hairpin RNA (shRNA) construct specific for the knockdown of furin, a proprotein convertase critically involved in the functional processing of all TGF-β isoforms. Prior work by the inventors has demonstrated the effectiveness of FANG in generating GM-CSF expression and TGF-β1 and TGF-β2 depletion in human cancer lines. The incorporation of a bi-functional shRNAfurin in combination with hGM-CSF into an autologous cell vaccine is demonstrated herein to promote and enhance the immune response based on its effect on the afferent limb of that immune response.

As used herein the term "bi-functional" refers to a shRNA having two mechanistic pathways of action, that of the siRNA and that of the miRNA (the guide strand being non-complementary to the mRNA transcript) or miRNA-like (the guide strand being complementary to the mRNA transcript). The term "traditional" shRNA refers to a DNA transcription derived RNA acting by the siRNA mechanism of action. The term "doublet" shRNA refers to two shRNAs, each acting against the expression of two different genes but in the "traditional" siRNA mode.

Survival of patients with advanced NSCLC, the most common cancer involving both men and women, is 7 months or less following treatment with second line chemotherapy. Limited survival benefit and toxicity related to the cancer and the treatment commonly forces patients to decline further therapy. Demonstration of safety and extensive clinical justification including examples of dramatic response related to "targeted" immune stimulation and suppression of endogenous immune inhibition using the novel, mature technology of the present invention described herein provides an opportunity for safe and potentially effective clinical assessment. The commercial expansion of the RNA interference technology and vaccine manufacturing of the present invention will provide a gateway opportunity into management of NSCLC and likely other solid tumors, notably melanoma, ovary, prostate cancer, colon cancer and breast cancer Overcoming immune tolerance with cancer vaccines is a promising but difficult quest. The prevailing hypotheses for immune tolerance, based primarily on animal studies, include the low immunogenicity of the tumor cells, the lack of appropriate presentation by professional antigen presenting cells, immune selection of antigen-loss tumor variants, tumor induced immunosuppression, and tumor-induced privileged site [1]. Nevertheless, recent clinical trials that are based on transgene-expressing whole cancer cell vaccines have yielded promising results [2-5]. Whole cancer cell vaccines can potentially elicit broad-based, polyvalent immune responses to both defined and undefined tumor antigens, thereby addressing the possibility of tumor resistance through downregulation and/or selection for antigen-loss variants [6, 7].

Dranoff and Jaffee have shown in animal models [8], that tumor cells genetically modified to secrete GM-CSF, as compared to other cytokines, consistently demonstrated the most potent induction of anti-tumor immunity. When integrated as a cytokine transgene, GM-CSF enhances presentation of cancer vaccine peptides, tumor cell lysates, or whole tumor cells from either autologous or established allogeneic tumor cell lines [9]. GM-CSF induces the differentiation of hematopoietic precursors into professional antigen presenting (APC) dendritic cells (DC) and attracts them to the site of vaccination [8, 10]. GM-CSF also functions as an adjuvant for the DC maturation and activational processes of tumor antigen capture, process and presentation, upregulates their expression of costimulatory molecules, and their ability to migrate to secondary lymphoid tissues for activation of CD4+, CD8+ T cells, CD1d restricted invariant natural killer T (NKT) cells, and antibody producing B cells [11].

Recently, Hodi [12] reported that GVAX vaccination, followed by periodic infusions of anti-CTLA-4 antibodies to modulate effector and T regulatory cell functions, can generate clinically meaningful antitumor immunity in a majority of metastatic melanoma patients. These findings are consistent with the thesis that vaccination with a GM-CSF-augmented autologous cancer vaccine can successfully generate an immune mediated tumor destruction, particularly when coupled with an adjuvant treatment that depletes FoxP3+ Tregs activity, enhances tumor expression of MHC class I A chain (MICA) thereby activating natural killer (NK) and T cells, and enhances central memory T-cell CD4+ and CD8+ response.

The FANG approach of the present invention is supported by the findings of the inventors in 10 patients' autologous vaccines, which demonstrated consistently TGF-β1 and TGF-β2 reductions and elevated GM-CSF levels (FIGS. 1A-1C and FIGS. 2A-2F). Soundness of the furin-depletion approach has been confirmed by proof of principle documentation with the furin inhibitor-decanoyl-Arg-Val-Lys-Arg-CMK (Dec-RVKR-CMK) (SEQ ID NO: 3) in cancer cell lines (CCL-247 colorectal, CRL-1585 melanoma lines). Dec-RVKR-CMK is a peptidyl chloromethylketone that binds irreversibly to the catalytic site of furin and blocks its activity [59]. Dec-RVKR-CMK either completely or partially reduces the activity of furin substrates BASE (β-site APP-cleaving enzyme), MT5-MMP), and Boc-RVRR-AMC (SEQ ID NO: 4) [60]. The present inventors found both TGF-β1 and TGF-β2 activity to be significantly reduced in CCL-247 and CRL-15985 cancer lines by specific immunoassay, confirming the effectiveness of furin blockade on TGF-β isoform expression.

The FANG plasmid (FIG. 19) used to transfect the autologous cells is derived from the TAG plasmid [74] by replacing the TGFβ2 antisense sequence with the bi-shRNAfurin DNA sequence. Otherwise these two plasmids are identical (confirmed by DNA sequencing). The bi-shRNAfurin consists of two stem-loop structures with miR-30a backbone; the first stem-loop structure has complete complementary guiding strand and passenger strand, while the second stem-loop structure has three by mismatches at positions 9 to 11 of the passenger strand (FIG. 4A). The inventors adopted a strategy of using a single targeted site for both cleavage and sequestration. The encoding shRNA is able to accommodate mature shRNA loaded onto more than one types of RISC [65]. The rationale for focusing on a single site is that multi-site targeting may increase the chance for "seed sequence" induced off-target effect [66]. The two stem-loop double stranded DNA sequence was assembled with 10 pieces of synthetic complementing and interconnecting oligonucleotides through DNA ligation. The completed 241 base pairs DNA with Bam HI sites at both ends was inserted into the Bam HI site of the TAG expression vector in place of the TGFβ2 antisense sequence. Orientation of the inserted DNA was screened by PCR primer pairs designed to screen for the shRNA insert and orientation. The FANG construct has a single mammalian promoter (CMV) that drives the entire cassette, with an intervening 2A ribosomal skip peptide between the GM-CSF and the furin bifunctional shRNA transcript, followed by a rabbit polyA tail. There is a stop codon at the end of the GM-CSF transcript. Insertion of picornaviral 2A sequences into mRNAs causes ribosomes to skip formation of a peptide bond at the junction of the 2A and downstream sequence, leading to the production of two proteins from a single open reading frame [67]. However, in the instances in which shRNA or antisense are being expressed as the second transcript (as examples), only the first transcript is translated. The inventors found that the 2A linker to be effective for generating approximately equal levels of GM-CSF and anti-TFG-β transcripts with the TAG vaccine, and elected to use the same design for FANG.

The inventors validated the applicability of siRNA-mediated furin-knockdown for inhibiting TGF-β isoform expression. Prospective siRNA targeting sites (FIG. 4B) in the furin mRNA sequence were determined by the published recommendations of Tuschl and colleagues and the additional selection parameters that integrates BLAST searches of the human and mouse genome databases [73]. siRNAs targeting eligible coding and 3'UTRs sites (FIG. 4B) were tested. Following lipofection of CCL-247, CRL-1585 U87 and H460 cells, each of the 6 siRNA$^{furin}$ constructs was shown to markedly reduce TGF-β1 and TGF-β2 levels in culture supernatants without adversely affecting cell survival. Thus siRNA-mediated furin knockdown is effective for the depletion of TGF-β1 and -β2 isoforms.

The present inventors attempted to detect endogenous Furin protein in cell lines via Western Blot and Flow Cytometry. Five different commercial antibodies were screened for Western Blot and one pre-labeled antibody was screened for Flow Cytometry. All studies yielded negative results. Upon further study of the commercially available antibodies, all idiotypes were developed against fragments (or peptides) of the Furin protein. The Western Blot studies demonstrated that the 60 kDa variant was preferentially detected in 4 of the 5 antibodies screened. The last antibody did not detect Furin protein under the Western Blot conditions tested. Control lysates provided by the commercial vendors produced similar results to in-house cell line samples. The pre-labeled antibody for Flow Cytometry did not demonstrate a significant shift in Furin staining (i.e., no positive Furin population identified). Therefore, the Flow Cytometry could not be used to demonstrate Furin knockdown.

As an alternative to Furin protein detection, the inventors also screened samples for Furin enzyme activity. Using a fluorometric based assay, cell lines were screened for the conversion of substrate (Pyr-Arg-Thr-Lys-Arg-AMC) (SEQ ID NO: 5) by Furin to release the fluorophore (AMC). However, the detected signal of released AMC was too low to accurately demonstrate significant knockdown of Furin enzyme activity. A second barrier to the assay is that the substrate is cleaved by all serine proteases in the subtilisin-like prohormone convertase (PC) family. Therefore, similar proteases that are not targeted by our FANG shRNA product would remain active and cleave the fluorogenic substrate in the assay, thus reducing the capability to detect Furin knockdown.

Other applications for the bi-functional shRNAfurin include: (1) Systemic delivery via a tumor (±tumor extracellular matrix (ECM)) selective decorated (targeted), stealthed bilamellar invaginated liposome (BIV) to enhance the efferent limb of the immune response; (2) Systemic delivery via a tumor selective decorated (targeted), stealthed bilamellar invaginated liposome (BIV) to directly subvert the tumor promoting/maintaining effects of furin target molecules including, but not limited to, TGFβ1. TGFβ2, TGFβ3, IGF-II, IGF-1R, PDGF A, and, in some tumor types, MT1-MMP; (3) Systemic delivery via a tumor selective decorated (targeted), stealthed bilamellar invaginated liposome (BIV) to directly subvert the NOTCH/p300 pathway in putative cancer stem cells; (4) Systemic delivery via a tumor selective decorated (targeted), stealthed bilamellar invaginated liposome (BIV) to inhibit activation of toxins associated with anthrax, Shiga, diphtheria, tetanus, botulism and Ebola and Marburg viruses and/or (5) Systemic and/or inhalational delivery of a bilamellar invaginated liposome (BIV) (±decoration and reversible masking/stealthing) to inhibit Pseudomonas exotoxin A production as an adjunct to antibiotic therapy in patients with diseases with heightened risk of Pseudomonas mediated morbidity and mortality, e.g., cystic fibrosis.

TGF-β Knockdown: Transforming growth factors beta (TGF-β) are a family of multifunctional proteins with well known immunosuppressive activities [13]. The three known TGF-β ligands (TGF-β1, β2, and β3) are ubiquitous in human cancers. TGF-β overexpression correlates with tumor progression and poor prognosis [14, 15]. Elevated TGF-β levels within the tumor microenvironment are linked to an anergic antitumor response [14, 16-21]. TGF-β inhibits GM-CSF induced maturation of DCs [22] and their expression of MHC class II and co-stimulatory molecules [23]. Ardeshna [24] showed that lipopolysaccharide (LPS)-induced maturation of monocyte-derived DCs involved activation of p38 stress-activated protein kinase (p38SAPK), extracellular signal-regulated protein kinase (ERK), phosphoinositide 3-OH— kinase (PI3 kinase)/Akt, and nuclear factor (NF)-κB pathways. GM-CSF can exert parallel activities of stimulating myeloid hematopoietic cell and leukemia cell line proliferation through rapid, transient phosphorylation of MAP kinase 1/2 and ERK 1/2, whereas TGF-β turns off GM-CSF-induced ERK signaling via PI3-kinase-Akt pathway inhibition [25].

At the efferent level, antigen presentation by immature DCs contributes to T cell anergy [26]. TGF-β similarly inhibits macrophage activation [27] and their antigen presenting function [28, 29]. TGF-β inhibits the activation of cytotoxic T cells by impairing high affinity IL-2 receptor expression and function [30, 31]. TGF-β2 also converts naïve T cells to Treg cells by induction of the transcription factor FOXP3 [32], with emergence of Treg leading to the shutdown of immune activation [33]. According to Polak [34], tolerogenic DCs and suppressor T lymphocytes were present in all stages of melanoma. These immune cell types expressed TGF-β receptor I, and tolerogenic activity was dependent on TGF-β1 or β2 binding.

At the innate immune response level, TGF-β is antagonistic on NK cells and down-regulates lymphokine activated killer (LAK) cell induction and proliferation [30, 35-39]. Penafuerte [40] recently showed that tumor-secreted TGF-β suppressed GM-CSF+IL2 (GIFT2) mediated immunosensitization of NK cells in the immunocompetent B16 melanoma model. In vivo blockade of B16 production of TGF-β improved survival otherwise compromised by the growth of non-GIFT2 expressing bystander tumors. These findings further validate the negative impact of TGF-β on GM-CSF-mediated immune activation in vivo, and by extension, support the rationale of depleting TGF-β secretion in GM-CSF-based cancer cell vaccines.

Trials conducted by the present inventors utilizing a tumor cell vaccine with TGF-β 2 knockdown activity (Belagenpumatucel-L) in patients with non-small cell lung cancer demonstrated acceptable safety, and a dose-related survival improvement in response to randomized control patients and historical experience. The two-year survival for the late stage (IIIB/IV) patients was 52% for patients who received >2.5× $10^7$ cells/injection, which compares favorably with similar patient historical data of less than 10% survival at 2 years. The study patients also displayed significantly elevated cytokine production (IFN-γ, p=0.006; IL-6, p=0.004; IL4, p=0.007) and antibody titers to vaccine HLA antigens (p=0.014), suggesting an immune activating outcome. [41].

TGF-β-knockdown and GM-CSF Expressive Cancer Cell Vaccine (TAG): Thirty six patients were harvested for TAG vaccine. GM-CSF expression and TGF-β2 knockdown met product release criteria. Three (all gastrointestinal tumors with luminal access) had bacterial contaminants and could not be released. One had insufficient cells. Nineteen advanced refractory cancer patients were treated [42-44]. No Grade 3 toxic effects related to therapy were observed. Eleven of 17 (65%) evaluable patients maintained stable disease for at least 3 months. One patient achieved CR by imaging criteria (FIG. 4; melanoma). Thus the TAG vaccine appears to be safe and has evidence of clinical efficacy.

A potential limitation of TAG vaccine, however, is the restricted specificity for TGF-β2, given that all three known isoforms of TGF-β ligand (TGF-β1, -β2, and -β3) are ubiquitously produced in human cancers. In particular, up to a 10-fold higher level of TGF-β1 may be produced by human colorectal, lung cancer, and melanoma cells. The tolerogenic role of TGF-131 in antigen presenting dendritic cells (DC) and regulatory T cells (Treg) is well established, and this activity is not impacted by TGF-β2 antisense treatment.

Furin: All mature isoforms of TGF-β require limited proteolytic cleavage for proper activity. The essential function of proteolytic activation of TGF-β is mediated by furin. Furin is a member of the subtilisin-like proprotein convertase family. The members of this family are proprotein convertases (PCs) that process latent precursor proteins into their biologically active products. Furin, a calcium-dependent serine endoprotease, efficiently cleaves precurson proteins at their paired basic amino acid processing sites by the consensus sequence -Arg-X-K/Arg-Arg (RXK/RR) (SEQ ID NO: 6), with -RXXR- (SEQ ID NO: 1) constituting the minimal cleavage site [53]. Like many other protases, PCs are synthesized as inactive zymogens with an N-terminal prosegment extension, which is autocatalytically removed in the endoplasmic reticulum to achieve functionality [52].

Furin is best known for the functional activation of TGF-β with corresponding immunoregulatory ramifications [54, 55]. Apart from the previously described immunosuppressive activities of tumor secreted TGF-β, conditional deletion of endogenous-expressing furin in T lymphocytes was found to allow for normal T-cell development, but impaired the function of regulatory and effector T cells, which produced less TGF-β1. Furin-deficient Tregs were less protective in a T-cell transfer colitis model and failed to induce Foxp3 in normal T cells. Additionally, furin-deficient effector cells were inherently over-active and were resistant to suppressive activity of wild-type Treg cells. In APCs, cytotoxic T lymphocyte-sensitive epitopes in the trans-Golgi compartment were processed by furin and the less frequented TAP independent pathway [56]. Thus furin expression by T cells appears to be indispensable in maintaining peripheral tolerance, which is due, at least in part, to its non-redundant, essential function in regulating TGF-β1 production.

High levels of furin have been demonstrated in virtually all cancer lines [45-52]. The present inventors and others have found that up to a 10-fold higher level of TGF-β1 may be produced by human colorectal, lung cancer, and melanoma cells, and likely impact the immune tolerance state by a higher magnitude [34, 57, 58]. The presence of furin in tumor cells likely contributes significantly to the maintenance of tumor directed, TGF-β1 mediated peripheral immune tolerance [54]. Hence furin knockdown represents a novel and attractive approach for optimizing immunosensitization.

FANG (furin shRNA and GMCSF) vaccine: The present inventors constructed the next generation vaccine termed FANG. The novelty of the FANG vaccine lies in the combined approach of depleting multiple immunosuppressive TGF-β isoforms by furin knockdown, in order to maximize the immune enhancing effects of the incorporated GM-CSF transgene on autologous tumor antigen sensitization.

All mature isoforms of TGF-β require proteolytic activation by furin. The feasibility of achieving concomitant depletion of multiple TGF-β isoform activity in several cancer cell lines (H460, CCL-247, CRL-1585, U87) was determined using furin-knockdown and the present inventors have successfully completed GMP manufacturing of FANG vaccine in 9 cancer patients (breast—1; colon—2; melanoma—4; gallbladder—1; NSCLC—1). Assessment of GMCSF expression and TGF-β1 and -β2 knockdown is shown in FIGS. 1A-1C and FIGS. 2A-2F.

Electroporation of FANG plasmid into patient tumor cells demonstrated GMCSF protein production and concomitantly TGF-β1 and -β2 knockdown as predicted. FIGS. 3A-3C depicts Day 7 assay data of a FANG-transfected NSCLC tumor's expression profile (FANG-004) versus tissue from the same the tumor processed by the cGMP TAG vaccine method (denoted TAG-004). There are similar reductions in TGFβ2 (FIG. 3B; single line shown due to coincident data) and similar increases in GMCSF (FIG. 3C) expression. However, while TGFβ1 expression is completely inhibited by FANG, it is unaffected by TAG as the TGFβ2 antisense cannot block TGFβ1 expression (FIG. 3A).

FIG. 5 is a PET CT image of an advanced melanoma patient after 11 TAG vaccine treatments demonstrating a significant clinical response. Residual uptake at L 2 was followed up with a MRI scan and biopsy which revealed no malignancy. The patient has consequently become a complete response (no evidence of disease) for greater than seven months. The capability of FANG to knockdown both TGF-β1 and -β2 is supported yb findings in the first 9 patients (FIGS. 6A-6C) who underwent vaccine construction. All 9 vaccine preparations demonstrated significantly elevated levels of GM-CSF (80-1870 pg/ml at day 4 of culture, median of 739 pg/ml). All 9 patients demonstrated >50% reductions of TGF-β2, and 6 of 7 patients with >100 pg of endogenous TGF-β1 production also demonstrated >50% reduction of this cytokine. The expanded target effectiveness of FANG is best demonstrated in one patient (NSCLC) who had adequate tumor tissue to generate both TAG (TAG-004A) and FANG (FANG-004) versions of autologous vaccine, TGF-β1 (as well as TGF-β2) was depleted to below detectable levels using the FANG preparation (FANG-004) from an initial concentration of 1840 pg/ml whereas this high level of TGF-β1 was unchanged with the TAG preparation (TAG-004) albeit with the expected depletion of TGF-β2. These findings support the potential advantage of the FANG vaccine preparation.

Validation of bioactivity of personalized cGMP FANG vaccines: Gene modification will be achieved by the use of a plasmid vector encoding for GM-CSF and a bi-functional short hairpin (bi-sh) RNA optimized for furin knockdown. Cancer patient autologous FANG vaccine has already been generated under cGMP conditions for clinical trial of patients with advanced solid cancers. GM-CSF and TGF-β1, -β2, and -β3 mRNA and protein expression were measured as part of the quality assurance process. Cytokine bioactivity following FANG modification was determined by growth outcome in a GM-CSF and TGF-β dependent cell line utilized by the present inventors in previous studies. Processed vaccine will undergo proteogenomic screening to verify antigenic integrity following FANG modification.

To characterize the augmenting effect of CTLA-4 blockade: Given that FANG immunization only impacts the afferent immunosensitization process, additional approaches that promote tumor-specific immune effector responses may further promote antitumor outcome. Disrupting Treg suppression and/or enhancing T effectors (Teff) by blockade of the cytotoxic T lymphocyte-4 (CTLA-4) function may enhance the likelihood of clinical success of the FANG vaccine.

RT-qPCR analysis was performed on ten FANG vaccine samples (FANG-003 did not have adequate mRNA for analysis). Samples were cultured pre-electroporation and post-electroporation, post-irradiation for up to 14 days. Total RNA was extracted from each sample at various time points and converted into cDNA via reverse transcription (RT). Quantitative PCR (qPCR) was performed to assess the amount of template present in each sample, at each time point. Furin, TGFβ1, and TGFβ2 qPCR samples were normalized to endogenous GapDH to produce a relative cycle threshold (Ct) value. GMCSF was quantified against an external standard curve to produce an absolute Ct value, relative to the standard curve. The GMCSF mRNA detection is shown in FIG. 7. Post-transfection, GMCSF mRNA is detected in all vaccines but the values are variable depending on mRNA quality—a persistent issue. Table 1 illustrates representative data from two FANG vaccines (FIGS. 8 and 9). All samples were calculated as normalized pre-electroporation Ct values minus normalized post-electroporation, post-irradiation Ct values (pre-post) to calculate the delta Ct (ΔCt). A calculated ΔCt <0.00 represents a decrease in template DNA and a calculated ΔCt >0.00 represents an increase in template DNA. The ΔCt value is used to estimate the percent change in expression (% expression). Values less than 100% represent a decrease in DNA (from pre to post) and values greater then 100% represent an increase in DNA (from pre to post). The nature of shRNA/siRNA silencing can optimally reduce the template DNA 90%, which is equivalent to a ΔCt=−3.3. (A ΔCt=−1.0 is equivalent to a 50% knockdown.) Therefore, the data below demonstrate that the FANG plasmid DNA is able to reduce endogenous Furin down 80-26% (average=48%) and the downstream targets TGFβ1 and TGFβ2 are reduced down 98-30% (average=75%). The mechanisms of action of the Furin bifunctional shRNA are to block Furin protein production at the post-transcriptional and translational levels. The reduced levels of Furin protein also impact (by feedback regulation) the expression of TGFβ1 and TGFβ2 mRNA, the conversion of the proform of TGFβ1 and TGFβ2 protein into the mature (active) form of their respective proteins [75], and, by interfering with the TGF→furin amplification loop, further dampen the expression of furin itself [76]. It is also possible that accumulation of the proform of the TGF protein may feedback inhibit the transcription of its TGF gene.

TABLE 1

RT-qPCR Analysis of FANG Vaccines (Pre Versus Post Electroporation)

| | FANG-008 | | | FANG-009 | |
|---|---|---|---|---|---|
| Furin Time Point | Δ Ct | % Expression | Furin Ident. | Δ Ct | % Expression |
| day 0 | −1.52 | 35% | day 0 | −0.66 | 63% |
| day 1 | −1.50 | 35% | day 1 | −0.69 | 62% |
| day 2 | −1.48 | 36% | day 2 | −0.34 | 79% |
| day 4 | −1.50 | 35% | day 4 | −0.31 | 80% |
| day 7 | −1.22 | 43% | day 7 | −1.93 | 26% |
| day 10 | −1.41 | 38% | day 10 | 0.00 | n/a * |
| TGFB1 Time Point | Δ Ct | % Expression | TGFB1 Ident. | Δ Ct | % Expression |
| day 0 | −0.09 | 94% | day 0 | −0.54 | 69% |
| day 1 | −0.10 | 93% | day 1 | −0.49 | 71% |
| day 2 | −0.08 | 95% | day 2 | −0.42 | 75% |
| day 4 | −0.05 | 97% | day 4 | −0.31 | 81% |
| day 7 | −0.08 | 95% | day 7 | −0.04 | 98% |
| day 10 | −0.11 | 93% | day 10 | −1.29 | 41% |
| TGFB2 Time Point | Δ Ct | % Expression | TGFB2 Ident. | Δ Ct | % Expression |
| day 0 | 0.00 | n/a * | day 0 | −0.53 | 69% |
| day 1 | 0.00 | n/a * | day 1 | −0.47 | 72% |
| day 2 | 0.00 | n/a * | day 2 | −0.45 | 73% |
| day 4 | 0.00 | n/a * | day 4 | −0.52 | 70% |
| day 7 | 0.00 | n/a * | day 7 | −1.70 | 31% |
| day 10 | 0.00 | n/a * | day 10 | −1.74 | 30% |

Δ Ct baseline = 0.00
% expression baseline = 100%
* n/a = not applicable because templatewas below detection limits The FANG system was used with 9 patient autologous vaccines, which consistently demonstrated TGF-β1 and TGF-β2 reductions and elevated GM-CSF levels (FIGS. 6A-6C). Both TGF-β1 and TGF-β2 activity by specific immunoassay was also demonstrated to be significantly reduced in these cancer lines, confirming the effect of furin blockade on TGF-β isoform expression. The inventors validated the applicability of siRNA-mediated furin-knockdown for inhibiting TGF-β isoform expression. Prospective siRNA targeting sites in the furin mRNA sequence (FIG. 4B) were determined by the published recommendations of Tuschl and colleagues and the additional selection parameters that integrated BLAST searches of the human and mouse genome databases (jura.wi.mit.edu/bioc/siRNAext). siRNAs targeting eligible translated and 3'UTRs sites (FIG. 4B) were tested. Demonstration of FANG plasmid DNA knockdown of furin mRNA is shown in FIGS. 8 and 9. This could only be detected in two of the vaccines because readily detectable furin mRNA was present in only these two tumors pretransfection. The mechanisms of action of the bi-shRNA$^{furin}$ are the blockade of furin protein production at the post transcriptional and translational levels. The reduced levels of furin protein also impact (by feed back regulation) the expression of TGF-β1 and TGF-β2 mRNA, the conversion of the proform TGF-β1 and TGF-β2 protein into the mature (active) form of their respective proteins [75] and by interfering with the TGF-β→furin loop, further dampening the expression of furin itself [76]. The possibility that the accumulation of the proform of the TGF protein may feedback and inhibit the transcription of its TGF gene should not be in any way construed as a limitation of the present invention. The expanded target effectiveness of FANG is best demonstrated in one patient (NSCLC) who had adequate tumor tissue to generate both TAG (TAG-004) and FANG (FANG-004) versions of autologous vaccine. TGF-β1 (as well as TGF-β2) was depleted to below detectable levels using the FANG preparation (FANG-004) from an initial concentration of 1840 pg/ml. This high level of TGF-β1 was unchanged with the TAG preparation (TAG-004) albeit with the expected depletion of TGF-β2 (FIGS. 1A-1C and FIGS. 2A-2F). These findings support the mechanistic advantage of the FANG vaccine preparation.

Following lipofection of CCL-247, CRL-1585 U87 and H460 cells, each of the 6 siRNAfurin constructs was shown to markedly reduce TGF-β1 and TGF-β2 levels in culture supernatants without adversely affecting cell survival. Thus siRNA-mediated furin knockdown is effective for the depletion of TGF-β1 and -β2 isoforms.

Design and construction of FANG: A "bi-functional" vector was used that incorporates both siRNA and miRNA-like functional components for optimizing gene knockdown [61]. The siRNA component is encoded as a hairpin and encompasses complete matching sequences of the passenger and guide strands. Following cleavage of the passenger strand by the Argonaute-2 (Ago 2) of the RNA-induced silencing complex (RISC), an endonuclease with RNase H like activity, the guide strand binds to and cleaves the complementary target mRNA sequence. In distinction, the miRNA-like component of the "bi-functional" vector incorporates mismatches between the passenger and guide strands within the encoding shRNA hairpin in order to achieve lower thermodynamic stability. This configuration allows the passenger strand to dissociate from RISC without cleavage (cleavage-independent process) independent of Ago 2 [62, 63], and the miRNA guide component to downregulate its target through translational repression, mRNA degradation, and sequestration of the partially complementary target mRNA in the cytoplasmic processing bodies (P-body).

The inventors have previously demonstrated the enhanced effectiveness of a bi-functional shRNA to knockdown stathmin (STMN1; oncoprotein 18), a protein that regulates rapid microtubule remodeling of the cytoskeleton and found to be upregulated in a high proportion of patients with solid cancers [64]. The bi-functional shRNA construct achieved effective knockdown against STMN-1 resulting in a 5-log dose enhanced potency of tumor cell killing as compared with siRNA oligonucleotides directed against the same gene target.

A similarly designed bi-functional shRNA was used to effect furin knockdown. The bi-sh-furin consists of two stem-loop structures with a miR-30a backbone; the first stem-loop structure has complete complementary guiding strand and passenger strand, while the second stem-loop structure has three by mismatches at positions 9 to 11 of the passenger strand. The inventors adopted a strategy of using a single targeted site for both cleavage and sequestration processes. The encoding shRNAs are proposed to allow mature shRNA to be loaded onto more than one type of RISC [65]. The inventors focused on a single site since multi-site targeting may increase the chance for "seed sequence" induced off-target effects [66].

The two stem-loop structure was put together with 10 pieces of complementing and interconnecting oligonucleotides through DNA ligation. Orientation of the inserted DNA was screened by PCR primer pairs designed to screen for the shRNA insert and orientation. Positive clones were selected and sequence confirmed at SeqWright, Inc. (Houston, Tex.). Based on siRNA findings, three bi-functional shRNA's were constructed. The optimal targeting sequence was identified.

The FANG construct has a single mammalian promoter (CMV) that drives the entire cassette, with an intervening 2A ribosomal skip peptide between the GM-CSF and the furin bi-functional shRNA transcripts, followed by a rabbit polyA tail. There is a stop codon at the end of the GM-CSF transcript.

Insertion of picornaviral 2A sequences into mRNAs causes ribosomes to skip formation of a peptide bond at the junction of the 2A and downstream sequences, leading to the production of two proteins from a single open reading frame [67]. The inventors found that the 2A linker to be effective for generating approximately equal levels of GM-CSF and anti-TGF-β transcripts with the TAG vaccine, and elected to use the same design for FANG.

Manufacturing the FANG vaccine: The patient's tumor was aseptically collected in the surgical field, placed in a gentamycin saline solution in a sterile specimen container and packaged for shipment on wet ice to the cGMP manufacturing facility. The specimen was brought into the manufacturing suite, dissected, enzymatically and mechanically disaggregated to form a cell suspension and then washed to remove debris. After the tumor cells are enumerated, QC aliquots are taken and the remaining cells are electroporated with the FANG plasmid and incubated overnight to allow vector transgene expression. Cells are harvested and gamma irradiated to arrest cell growth, then enumerated prior to removal of final QC aliquots and vaccine controlled rate freezing. The two day manufacturing process was followed by an almost three week QC testing phase after which all of vaccine assay data are evaluated prior to releasing the vaccine for patient treatment. All 9 initial patients who underwent FANG manufacturing passed all QC testing criteria.

cGMP FANG vaccines: Cancer patient autologous FANG vaccines were generated under cGMP conditions for use in clinical trials. GM-CSF and TGF-β1, -β2, and -β3 mRNA and protein expression were measured before and after FANG modification, and cytokine bioactivity determined by growth outcome on a GM-CSF and TGF-β dependent human cell line we have previously characterized. Each patient's processed vaccine will undergo proteogenomic screening to verify antigenic integrity following FANG modification.

cGMP production of FANG: FANG vaccine was generated by plasmid vector electroporation of established human cell lines. The selected FANG plasmid vector represents a construct containing the furin shRNA that has been prevalidated for optimal TGF-β downregulation.

Before being injected into patients, a frozen vial (dose) was thawed at room temperature and processed in a biosafety hood. The cell suspension will be delivered in a capped 1 mL syringe. The prepared vaccine will be injected intradermally into patient at a dose of $1 \times 10^7$ or $2.5 \times 10^7$ cells per injection.

Two full scale preclinical manufacturing processes and eight clinical manufacturing processes were prepared and studies by the present inventors. Table 2 depicts the types of tumors processed (tumors 3 through 10 are the clinical vaccines).

TABLE 2

Tumor mass versus cell yield.

| Tumor Processed | Vaccine ID | Tissue Weight (grams) | Cell #/dose | Number of Vials |
|---|---|---|---|---|
| 1 | FANG-001 | 12.72 | $1.0 \times 10^7$ | 40 |
| 2 | FANG-002 | 27.41 | $1.0 \times 10^7$ | 28 |
| 3 | FANG-003 | 6.04 | $2.5 \times 10^7$ | 9 |
| 4 | FANG-004 | 41.08 | $2.5 \times 10^7$ | 11 |
| 5 | FANG-005 | 6.96 | $2.5 \times 10^7$ | 8 |
| 6 | FANG-006 | 12.48 | $1.0 \times 10^7$ | 8 |
| 7 | FANG-007 | 10.90 | $2.5 \times 10^7$ | 15 |
| 8 | FANG-008 | 9.80 | $2.5 \times 10^7$ | 13 |
| 9 | FANG-009 | 6.80 | $1.0 \times 10^7$ | 6 |
| 10 | FANG-010 | 13.00 | $2.5 \times 10^7$ | 12 |

The tumors processed range in size, as well as type, and the resulting viable cell yield varies greatly as shown in Table 3. All vaccines are vialed at either $1.0 \times 10^7$ cells (dose Cohort 1) or $2.5 \times 10^7$ cells (dose Cohort 2) depending on the total viable cell count on Day 2 of manufacturing. Patients with multiple tumor harvests were allowed to combine vials to qualify for minimum clinical dose requirement. A maximum of 12 doses at Cohort 2 dose level will be made available for patient treatment. Because tumor cell yield is highly variable due to tumor mass, cellularity, and processing compatibility, the minimum dose number and lower dose cohort (Cohort 1) were included.

TABLE 3

Final product viability (Day 2, Pre Irradiation)

| Tumor Processed | Vaccine ID | % Viability |
|---|---|---|
| 1 | FANG-001 | 78 |
| 2 | FANG-002 | 90 |
| 3 | FANG-003 | 94 |
| 4 | FANG-004 | 89 |
| 5 | FANG-005 | 94 |
| 6 | FANG-006 | 91 |
| 7 | FANG-007 | 96 |
| 8 | FANG-008 | 95 |
| 9 | FANG-009 | 95 |
| 10 | FANG-010 | 93 |

Figure 1A:
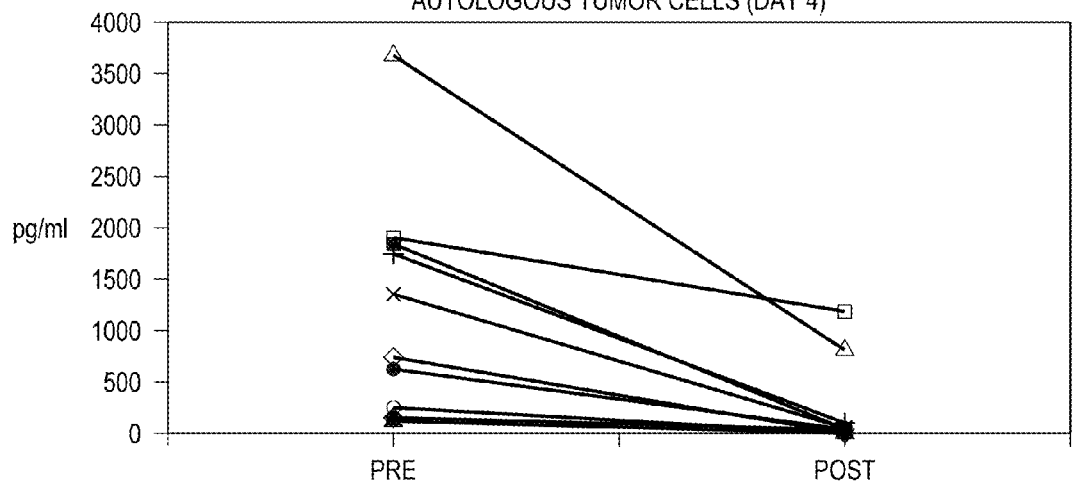
FIGS. 1A-1C are plots showing the summary of: (1A) TGF-β1, (1B)-β2, and (1C) GMCSF protein production pre and post FANG plasmid transfection. ELISA values from Day 4 of the 14-day determinations of cytokine production in manufactured autologous cancer cells. Data represents autologous vaccines independently generated from 10 patients who underwent FANG processing (FANG 001-010).
Figure 1B:
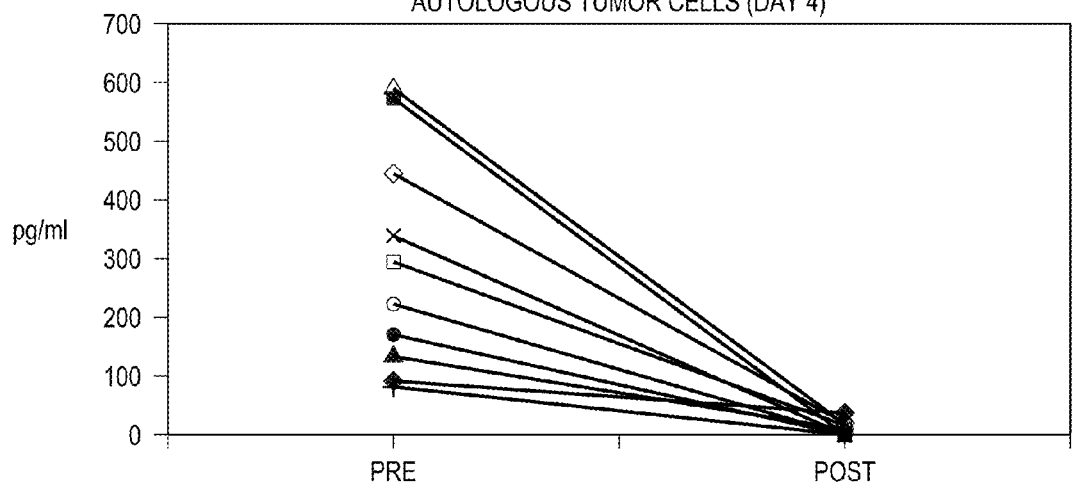
Figure 1C:
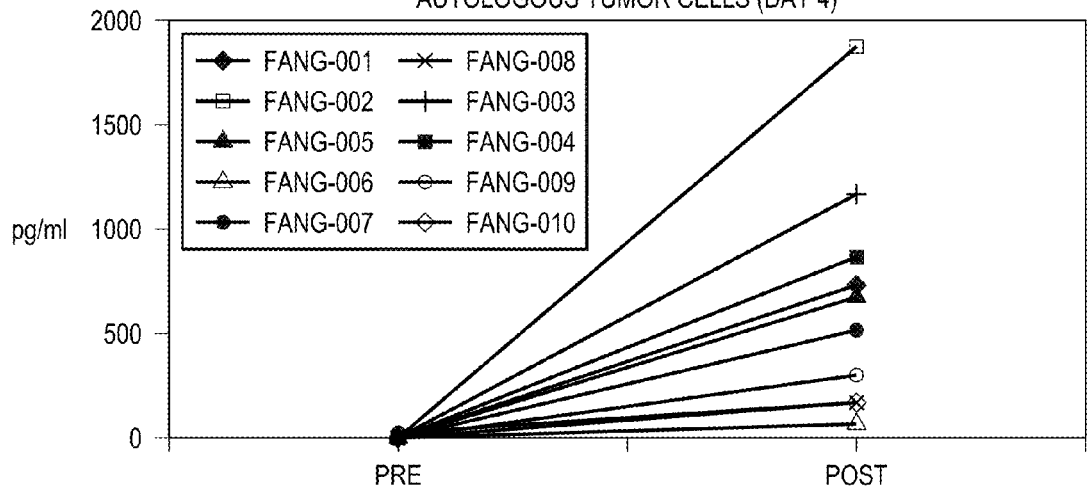
Figure 2A:
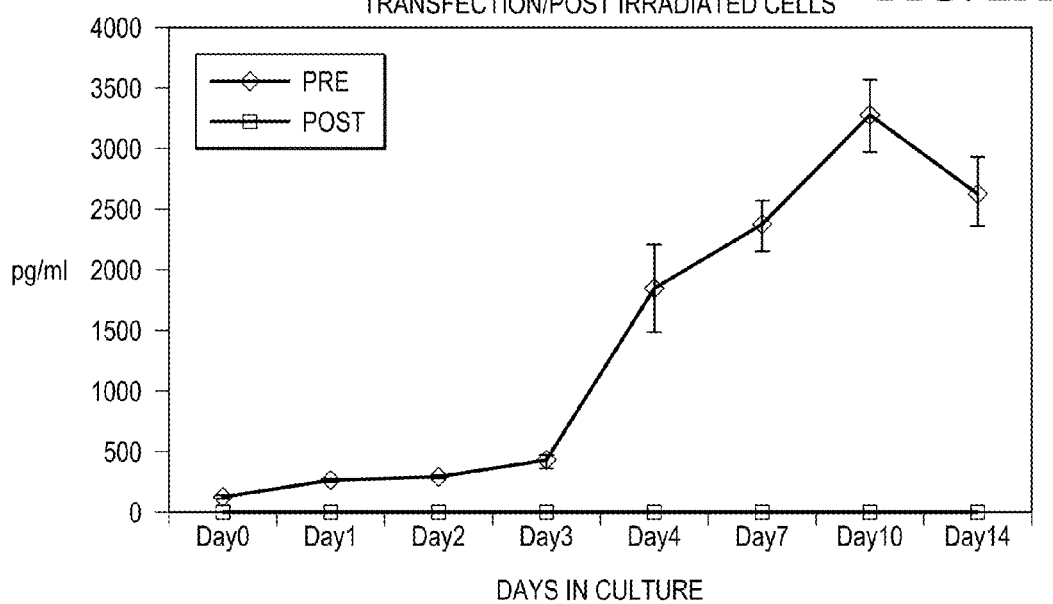
Figure 2B:
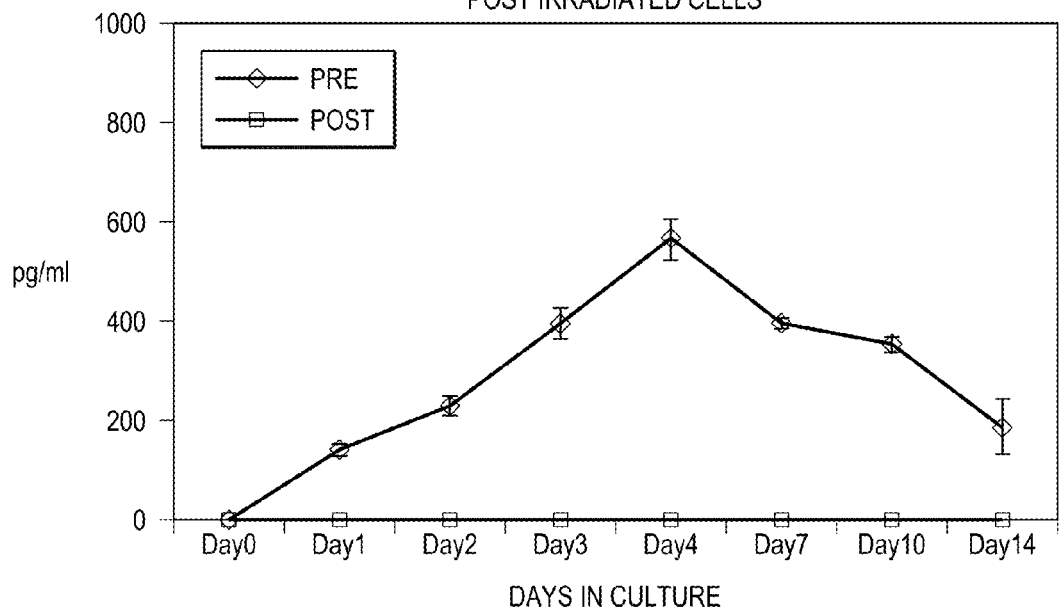
Figure 2C:
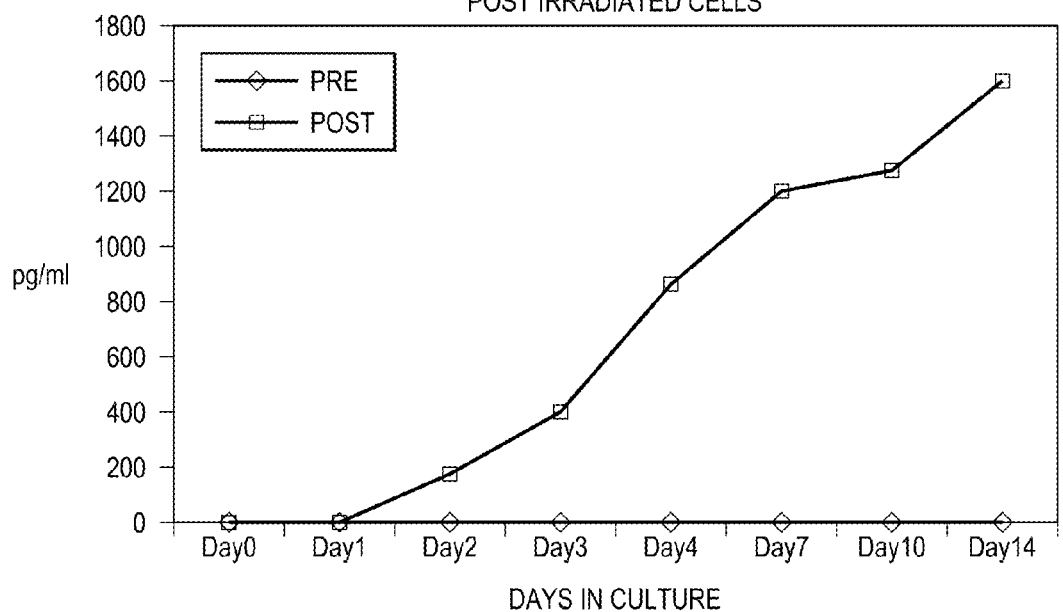
Figure 2D:
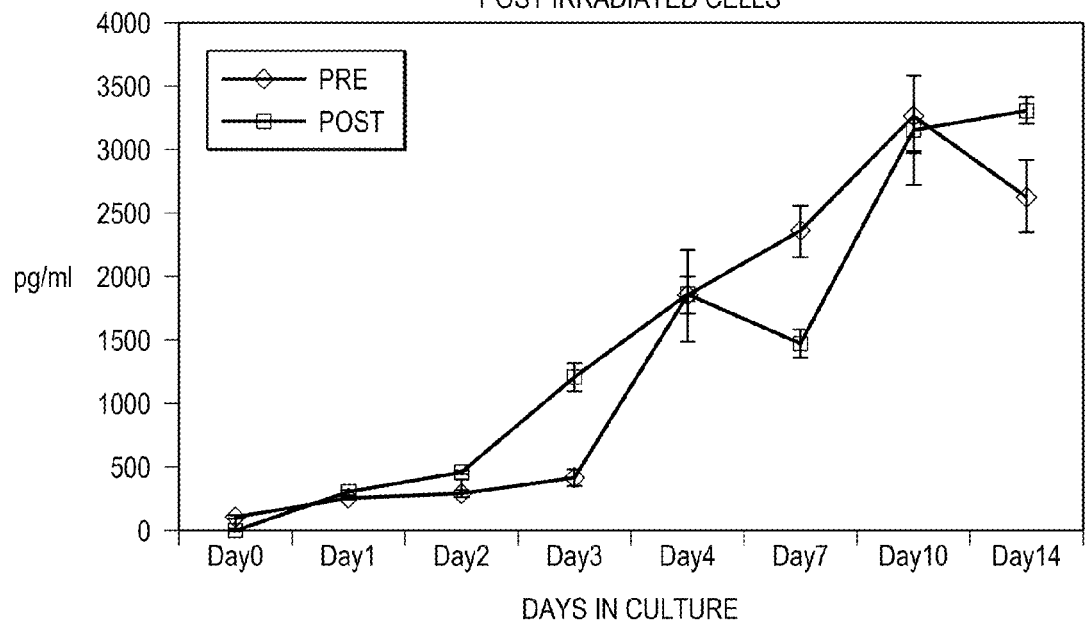
Figure 2E:
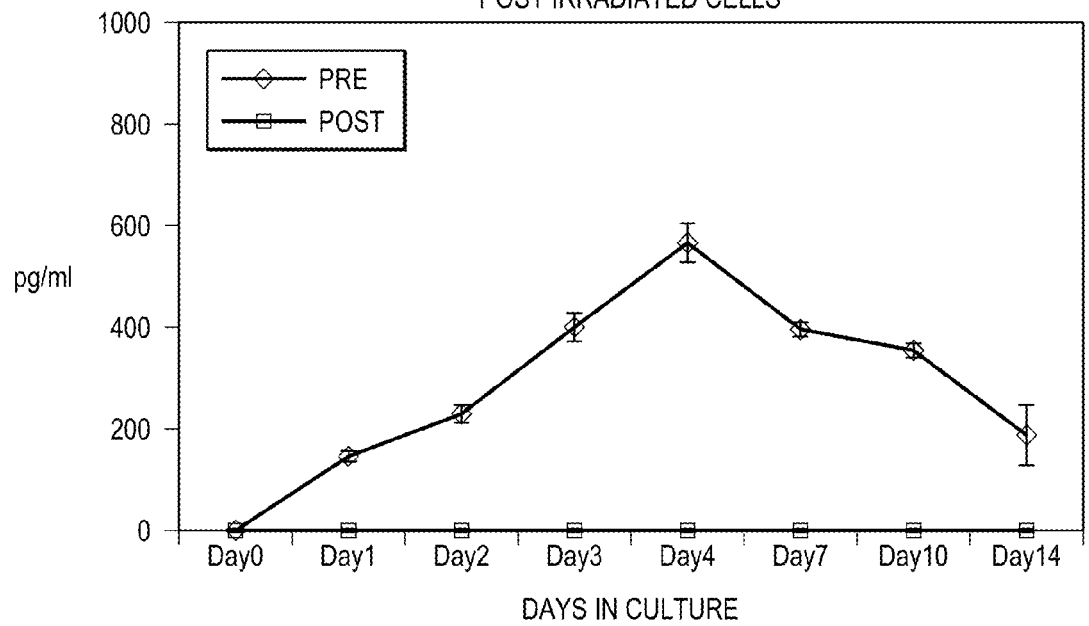

The Day 4 expression profiles of the 10 tumors processed are depicted in FIGS. 1A-1C. Note that the y-axis scales are different for all three cytokines. These data are representative of the 14 day assay (remainder of data not shown). The mean pretransfection TGFβ1 is 1251±1544 pg/1×10$^6$ cells/ml; median 778 pg. The mean posttransfection TGFβ1 is 191±455 pg/1×10$^6$ cells/ml; median 13 pg. The average percent knockdown of TGFβ1 was 85%. The mean pretransfection TGFβ2 is 232±164 pg/1×10$^6$ cells/ml; median 225 pg. The mean posttransfection TGFβ2 is 1319 pg/1×10$^6$ cells/ml; median 5 pg. The average percent knockdown of TGFβ2 was 94%. The average GM-CSF expression post transfection is 543±540 pg/1×10$^6$ cells/ml; median 400 pg. These data indicate that the GMCSF expression is consistent with the TAG vaccine as is the TGF β2 knockdown. In contrast, FANG vaccines have reduced the TGFβ1 expression more than fivefold. The minimum detectable quantity of TGFβ1 is approximately 4.6 pg/ml (R&D Systems, Quantikine Human TGFβ1). The minimum detectable quantity of TGFβ2 is approximately 7 pg/ml (R&D Systems, Quantikine Human TGFβ2). The minimum detectable quantity of GMCSF is approximately 3 pg/ml (R&D Systems, Quantikine Human GMCSF).

transfection sample (4×10$^6$ cells) is taken on Day 1. After manufacturing is completed, the sample is removed from the manufacturing facility so that the cell cultures can be set up for generating the sample for ELISA. On Day 2, the post-transfection, post-irradiation, pre-freeze sample (4×10$^6$ cells) is taken. After manufacturing is completed, the sample is removed from the manufacturing facility so that the cell cultures can be set up for generating the sample for ELISA.

Ten (10) vaccines (FANG-001 to -010) have been manufactured as part of the preclinical qualification process. These vaccines have been evaluated for GM-CSF, TGFβ1 and TGFβ2 mRNA and protein expression using post-transfection, post-irradiation samples compared with pre-transfection, pre-irradiation samples (per FDA review, TAG vaccine, BB-IND 13650). In addition, Furin protein detection was attempted by several methods. Furin mRNA was detected by qRT-PCR.

The present inventors detected endogenous Furin protein in cell lines via Western Blot and Flow Cytometry. Five (5) different antibodies (from 3 different vendors) were screened for Western Blot and one (1) pre-labeled antibody was screened for Flow Cytometry. All experiments yielded negative results (data not shown).

A summary of all ELISA data for all manufacturing processes (Table 4) indicates that the median level of GMCSF expression is about 400 picogram/ml and the average is 543 picograms/ml. Further, the level of GMCSF tends to increase with time. In all manufactured products, GMCSF expression is observed although the level of expression is variable between manufacturing processes (tumor types). In addition to documented variability in the level of GMCSF expression between manufacturing processes, the levels of expression achieved with the FANG vaccine are deemed clinically relevant as 1) use of a plasmid rather than a viral vector obviates the obfuscating effects of elicited anti-viral neutralizing antibodies, 2) use of a plasmid likewise prevents the development of elicited antibodies interfering with long-term gene expression, and 3) concurrent suppression of furin, TGFβ1, and TGFβ2 will minimize tumor associated inhibition of GMCSF induced dendritic cell maturation [25].

Table 4: FANG vaccines 1-10 TGFβ1, TGFβ2 and GM-CSF expression in the 14 day 30 post manufacturing expression assay.

TABLE 4

FANG vaccines 1-10 TGFβ1, TGFβ2 and GM-CSF expression in the 14 Day post manufacturing expression assay.

| | TGFβ1 pg/ml Pre | | | TGFβ1 pg/ml Post | | | TGFβ2 pg/ml Pre | | | TGFβ2 pg/ml Post | | | GMCSF pg/ml Pre | | | GMCSF pg/ml Post | | |
|---|---|---|---|---|---|---|---|---|---|---|---|---|---|---|---|---|---|---|
| | Mean | SD | Median | Mean | SD | Median | Mean | SD | Median | Mean | SD | Median | Mean | SD | Median | Mean | SD | Median |
| Day 0 | 625 | 678 | 415 | 105 | 202 | 7 | 70 | 118 | 25 | 9 | 22 | 0 | 2 | 2 | 2 | 157 | 277 | 23 |
| Day 1 | 1154 | 1268 | 760 | 83 | 187 | 11 | 138 | 138 | 113 | 8 | 18 | 0 | 3 | 4 | 3 | 358 | 468 | 281 |
| Day 2 | 938 | 1014 | 620 | 180 | 446 | 8 | 189 | 107 | 187 | 12 | 21 | 4 | 3 | 3 | 3 | 487 | 418 | 316 |
| Day 3 | 1832 | 3221 | 878 | 173 | 384 | 4 | 247 | 155 | 229 | 12 | 15 | 8 | 3 | 4 | 2 | 580 | 531 | 475 |
| Day 4 | 1241 | 1115 | 1035 | 211 | 421 | 20 | 293 | 185 | 257 | 9 | 12 | 4 | 4 | 6 | 3 | 687 | 350 | 602 |
| Day 7 | 1723 | 1738 | 778 | 261 | 723 | 3 | 292 | 150 | 235 | 14 | 15 | 6 | 5 | 3 | 3 | 683 | 681 | 471 |
| Day 10 | 1367 | 894 | 1629 | 243 | 530 | 21 | 335 | 135 | 310 | 23 | 21 | 28 | 5 | 8 | 4 | 745 | 546 | 873 |
| Day 14 | 1108 | 692 | 887 | 281 | 681 | 19 | 304 | 158 | 239 | 17 | 23 | 12 | 18 | 24 | 4 | 821 | 531 | 845 |
| Overall | 1251 | 1544 | 778 | 191 | 458 | 13 | 232 | 164 | 225 | 13 | 19 | 5 | 5 | 10 | 3 | 543 | 540 | 425 |

The protocol for setting up cultures pre and post Transfection for Autologous tumor cell vaccine to test for the expression of GMCSF, TGFβ1 and TGFβ2 has been previously described (Maples, et al., 2009). Briefly, GMCSF, TGFβ1 and TGFβ2 expression were determined by commercially available ELISA kits (R & D Systems). The ELISA assays were performed according to manufacturer's instruction. The pre- Quantification of GM-CSF and TGF-β expressions: GM-CSF and TGF-β1 and -β2 expression was determined by cytokine specific colorimetric assay [68].

Validation of bioactivity: GM-CSF-induced proliferative activity similar to that of myeloid hematopoietic cells has been observed in myeloid leukemia cell lines, as mediated by the rapid and transient phosphorylation of MAP kinase 1/2 and ERK 1/2. By contrast, TGF-β turns off GM-CSF-mediated ERK signaling by inhibition of the PI3-kinase-Akt pathway [25]. The growth regulatory effects of GM-CSF and TGF-β on myeloid leukemic cells were used as an in vitro surrogate model to validate cytokine bioactivity in prepared FANG vaccine culture supernatants.

Cytokine activities in the FANG (or control-transfected) vaccine culture supernatants were validated by co-culture studies with erythroleukemic CD34+ TF-1a cells [69] and, if necessary, confirmed with the biphenotypic B myelomonocytic leukemic CD10+CD15+MV4-11 cells [70] (ATCC, Rockville, Md.). Both of these cell lines have been shown respond to the positive proliferative effects of GM-CSF and the negative inhibitory activity of TGF-β at ng/ml amounts [25]. Proliferative activity will be determined by Easycount Viasure assay (Immunicon) and MTT assay [68].

Phenotypic profile analysis of FANG modification: Furin knockdown likely impacts the expression of other protein substrates with the target sequence in addition to TGF-β downregulation [51]. The antigenic profile of the FANG-processed autologous vaccines were determined from cancer patients, in the event that this information may be useful towards the understanding any differential clinical outcome in vaccinated patients.

High throughput genetic profiling was used to develop individualized therapeutics for cancer patients. High throughput, gene expression array analysis was carried out to compare the differential gene expression profile of FANG-transfected vs. control vector-transfected cancer cells.

Differentially labeled FANG and control preparations are combined and fractionated by high performance liquid chromatography (Dionex), using a strong cation exchange column (SCX) and a $2^{nd}$ dimension RP nano column. The fractions are spotted onto Opti-TOF™ LC/MALDI Insert (123×81 mm) plates (Applied Biosystems) in preparation for mass spectrometry analysis using the Applied Biosystems 4800 MALDI TOF/TOF™ Analyzer. Both protein and gene expression data were then evaluated by the GeneGo, MetaCore software suite.

Proteogenomic analysis was carried out for the purpose of determining the antigen repertoire of the autologous cancer vaccine before and after FANG process. In addition to the validation of furin knockdown, particular attention was focused on 1) baseline and differential expression of furin-substrate proteins; 2) expression of landmark tumor-associated antigens (TAAs; such as gp100, Marti, MAGE-1, tyrosinase, for melanoma; MAGE-3, MUC-1 for non-small cell lung cancer) [71, 72] and other reported TAAs; 3) HLA antigens and co-stimulatory molecules (CD80/86) expression; 4) proteins unrelated to the above categories that are differentially expressed by 2-fold or higher following FANG transfection.

FIG. 10 shows the overall survival for Cohort 1 versus Cohorts 2 and 3 for advanced-stage patients (n=61; P=0.0186). A schematic diagram of GM-CSF-TGF-β2 antisense plasmid is shown in FIG. 11. The expression of GM-CSF in NCI-H-460 Squamous Cell and NCI-H-520, Large Cell (NSCLC) containing the pUMVC3-GM-CSF-2A-TGF-β2 antisense vector, in vitro is depicted in FIG. 12. TGF-β2 levels are reduced in NCI-H-460 Squamous Cell and NCI-H-520, Large Cell (NSCLC) with the pUMVC3-GM-CSF-2A-TGF-β2 antisense vector. This reduction is seen in the date presented in FIG. 13. FIG. 14 shows that a 251 base pair probe specifically detects the GM-CSF-2A-TGF-β2 transcript expressed in vitro in NCI-H-460 and NCI-H-520 cells (lanes 6 and 10); GM-CSF and TGF-β2 expression in TAG vaccines are shown in FIGS. 12 and 13, respectively. Expression of TGF-β1 and TGF-β2 in human cancer lines following siRNAfurin knockdown is shown in FIGS. 18A and 18B. Finally FIG. 19 is a schematic of the plasmid construct of FANG.

TGFβ1 expression data (FIG. 16) generated from TAG vaccine manufacturing data (n=33 vaccines; Day 7 values, TGFβ1 assay post vaccine manufacturing) clearly demonstrate that TAG does not interfere with TGFβ1 expression. The clinical significance of blocking TGFβ1 and TGFβ2 (FIG. 17), as well as TGFβ3 (data not shown) is that they are postulated to be significant negative immunomodulators expressed by the tumor. GM-CSF expression in TAG vaccines is shown in FIG. 15. These TGFβ isoforms are ubiquitous and expressed in the majority of tumors [77]. Many tumors, including breast, colon, esophageal, gastric, hepatocellular, pancreatic, SCLC and NSCLC produce high levels of one or more active TGFβ3 isoforms [78, 14, 15, 79-84]. Furthermore, overexpression of TGFβ3 has been correlated with tumor progression and poor prognosis [14, 15]. Elevated TGFβ3 levels have also been linked with immunosuppression in both afferent efferent limbs [14, 16-21]. Additionally, TGFβ3 has antagonistic effects on Natural Killer (NK) cells as well as the induction and proliferation of lymphokine-activated killer (LAK) cells [30, 35-39].

The immune suppressor functions of TGFββ are therefore likely to play a major role in modulating the effectiveness of cancer cell vaccines. TGFβ inhibits GMCSF induced maturation of bone marrow derived dendritic cells (DCs) [22] as well as expression of MHC class II and co-stimulatory molecules [23]. It has been shown that antigen presentation by immature DCs result in T cell unresponsiveness [26]. TGFβ also inhibits activated macrophages [27] including their antigen presenting function [28, 29]. Hence both the ubiquity of expression as well as the inhibitory effects of TGFβ on GMCSF immunomodulatory function support the knockdown of all tumor TGFβ expression in the autologous cancer vaccine treatment approach of the present invention.

The immune suppressor functions of TGFβ are therefore likely to play a major role in modulating the effectiveness of cancer cell vaccines. TGFβ inhibits GMCSF induced maturation of bone marrow derived dendritic cells (DCs) [25] as well as expression of MHC class II and co-stimulatory molecules [26]. It has been shown that antigen presentation by immature DCs result in T cell unresponsiveness [27]. TGFβ also inhibits activated macrophages [28] including their antigen presenting function [29, 30]. Hence both the ubiquity of expression as well as the inhibitory effects of TGFβ on GMCSF immunomodulatory function support the knockdown of all tumor TGFβ expression in this autologous cancer vaccine treatment approach.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Murphy, K., Travers, P., Walport, M., ed. Janeway's Immunobiology. 7th ed. 2008, Garland Science New York. 674-687.
2. Fakhrai, H., et al., Phase I clinical trial of a TGF-beta antisense-modified tumor cell vaccine in patients with advanced glioma. Cancer Gene Ther, 2006. 13(12): p. 1052-60.
3. Nemunaitis, J., GVAX (GMCSF gene modified tumor vaccine) in advanced stage non small cell lung cancer. J Control Release, 2003. 91(1-2): p. 225-31.
4. Nemunaitis, J., et al., Phase 1/2 trial of autologous tumor mixed with an allogeneic GVAX vaccine in advanced-stage non-small-cell lung cancer. Cancer Gene Ther, 2006. 13(6): p. 555-62.
5. Nemunaitis, J. and J. Nemunaitis, A review of vaccine clinical trials for non-small cell lung cancer. Expert Opin Biol Ther, 2007. 7(1): p. 89-102.
6. Ahmad, M., R. C. Rees, and S. A. Ali, Escape from immunotherapy: possible mechanisms that influence tumor regression/progression. Cancer Immunol Immunother, 2004. 53(10): p. 844-54.
7. Hege, K. M., K. Jooss, and D. Pardoll, GM-CSF gene-modified cancer cell immunotherapies: of mice and men. Int Rev Immunol, 2006. 25(5-6): p. 321-52.
8. Dranoff, G., et al., Vaccination with irradiated tumor cells engineered to secrete murine granulocyte-macrophage colony-stimulating factor stimulates potent, specific, and long-lasting anti-tumor immunity. Proc Natl Acad Sci USA, 1993. 90(8): p. 3539-43.
9. Hege, K. M. and D. P. Carbone, Lung cancer vaccines and gene therapy. Lung Cancer, 2003. 41 Suppl 1: p. S103-13.
10. Huang, A. Y., et al., Role of bone marrow-derived cells in presenting MHC class I-restricted tumor antigens. Science, 1994. 264(5161): p. 961-5.
11. Banchereau, J., et al., Immunobiology of dendritic cells. Annu Rev Immunol, 2000. 18: p. 767-811.
12. Hodi, F. S., et al., Immunologic and clinical effects of antibody blockade of cytotoxic T lymphocyte-associated antigen 4 in previously vaccinated cancer patients. Proc Natl Acad Sci USA, 2008. 105(8): p. 3005-10.
13. Wick, W., U. Naumann, and M. Weller, Transforming growth factor-beta: a molecular target for the future therapy of glioblastoma. Curr Pharm Des, 2006. 12(3): p. 341-9.
14. Bierie, B. and H. L. Moses, Tumour microenvironment: TGFbeta: the molecular Jekyll and Hyde of cancer. Nat Rev Cancer, 2006. 6(7): p. 506-20.
15. Levy, L. and C. S. Hill, Alterations in components of the TGF-beta superfamily signaling pathways in human cancer. Cytokine Growth Factor Rev, 2006. 17(1-2): p. 41-58.
16. Sporn, M. B., et al., Transforming growth factor-beta: biological function and chemical structure. Science, 1986. 233(4763): p. 532-4.
17. Massague, J., The TGF-beta family of growth and differentiation factors. Cell, 1987. 49(4): p. 437-8.
18. Bodmer, S., et al., Immunosuppression and transforming growth factor-beta in glioblastoma. Preferential production of transforming growth factor-beta 2. J Immunol, 1989. 143(10): p. 3222-9.
19. Border, W. A. and E. Ruoslahti, Transforming growth factor-beta in disease: the dark side of tissue repair. J Clin Invest, 1992. 90(1): p. 1-7.

20. Chen, T. C., et al., TGF-B2 and soluble p55 TNFR modulate VCAM-1 expression in glioma cells and brain derived endothelial cells. J Neuroimmunol, 1997. 73(1-2): p. 155-61.
21. Li, M. O., et al., Transforming growth factor-beta regulation of immune responses. Annu Rev Immunol, 2006. 24: p. 99-146.
22. Yamaguchi, Y., et al., Contrasting effects of TGF-beta 1 and TNF-alpha on the development of dendritic cells from progenitors in mouse bone marrow. Stem Cells, 1997. 15(2): p. 144-53.
23. Geissmann, F., et al., TGF-beta 1 prevents the noncognate maturation of human dendritic Langerhans cells. J Immunol, 1999. 162(8): p. 4567-75.
24. Ardeshna, K. M., et al., The PI3 kinase, p38 SAP kinase, and NF-kappaB signal transduction pathways are involved in the survival and maturation of lipopolysaccharide-stimulated human monocyte-derived dendritic cells. Blood, 2000. 96(3): p. 1039-46.
25. Montenegro, D. E., et al., TGFbeta inhibits GM-CSF-induced phosphorylation of ERK and MEK in human myeloid leukaemia cell lines via inhibition of phosphatidylinositol 3-kinase (PI3-k). Cell Prolif, 2009. 42(1): p. 1-9.
26. Steinman, R. M., et al., Dendritic cell function in vivo during the steady state: a role in peripheral tolerance. Ann N Y Acad Sci, 2003. 987: p. 15-25.
27. Ashcroft, G. S., Bidirectional regulation of macrophage function by TGF-beta. Microbes Infect, 1999. 1(15): p. 1275-82.
28. Du, C. and S. Sriram, Mechanism of inhibition of LPS-induced IL-12p40 production by IL-10 and TGF-beta in ANA-1 cells. J Leukoc Biol, 1998. 64(1): p. 92-7.
29. Takeuchi, M., P. Alard, and J. W. Streilein, TGF-beta promotes immune deviation by altering accessory signals of antigen-presenting cells. J Immunol, 1998. 160(4): p. 1589-97.
30. Ruffini, P. A., et al., Factors, including transforming growth factor beta, released in the glioblastoma residual cavity, impair activity of adherent lymphokine-activated killer cells. Cancer Immunol Immunother, 1993. 36(6): p. 409-16.
31. Fakhrai, H., et al., Eradication of established intracranial rat gliomas by transforming growth factor beta antisense gene therapy. Proc Natl Acad Sci USA, 1996. 93(7): p. 2909-14.
32. Fantini, M. C., et al., Cutting edge: TGF-beta induces a regulatory phenotype in CD4+CD25- T cells through Foxp3 induction and down-regulation of Smad7. J Immunol, 2004. 172(9): p. 5149-53.
33. Thomas, D. A. and J. Massague, TGF-beta directly targets cytotoxic T cell functions during tumor evasion of immune surveillance. Cancer Cell, 2005. 8(5): p. 369-80.
34. Polak, M. E., et al., Mechanisms of local immunosuppression in cutaneous melanoma. Br J Cancer, 2007. 96(12): p. 1879-87.
35. Rook, A. H., et al., Effects of transforming growth factor beta on the functions of natural killer cells: depressed cytolytic activity and blunting of interferon responsiveness. J Immunol, 1986. 136(10): p. 3916-20.
36. Kasid, A., G. I. Bell, and E. P. Director, Effects of transforming growth factor-beta on human lymphokine-activated killer cell precursors. Autocrine inhibition of cellular proliferation and differentiation to immune killer cells. J Immunol, 1988. 141(2): p. 690-8.
37. Tsunawaki, S., et al., Deactivation of macrophages by transforming growth factor-beta. Nature, 1988. 334(6179): p. 260-2.
38. Hirte, H. and D. A. Clark, Generation of lymphokine-activated killer cells in human ovarian carcinoma ascitic fluid: identification of transforming growth factor-beta as a suppressive factor. Cancer Immunol Immunother, 1991. 32(5): p. 296-302.
39. Naganuma, H., et al., Transforming growth factor-beta inhibits interferon-gamma secretion by lymphokine-activated killer cells stimulated with tumor cells. Neurol Med Chir (Tokyo), 1996. 36(11): p. 789-95.
40. Penafuerte, C. and J. Galipeau, TGF beta secreted by B16 melanoma antagonizes cancer gene immunotherapy bystander effect. Cancer Immunol Immunother, 2008. 57(8): p. 1197-206.
41. Nemunaitis, J., et al., Phase II trial of Belagenpumatucel-L, a TGF-beta2 antisense gene modified allogeneic tumor vaccine in advanced non small cell lung cancer (NSCLC) patients. Cancer Gene Ther, 2009. 16(8): p. 620-4.
42. Maples PB, K. P., Oxendine I, Jay C, Yu Y, Kuhn J, Nemunaitis J, TAG Vaccine: Autologous Tumor Vaccine Genetically Modified to Express GM-CSF and Block Production of TGFB2. BioProcessing Journal, 2009. 8(2).
43. Nemunaitis, J., Kumar, P., Senzer, N., Yu, Y., Oxendine, I., Tong, A. W., Maples, P. B., A phase I trial of GMCSF gene-TGFbeta antisense gene autologous tumor cell (TAG) vaccine in advanced cancer. Mol Therapy, 2009. 17 (Suppl 1): p. S206.
44. Maples, P. B., et al. Autologous Tumor Cell Vaccine Genetically Modified To Express GM-CSF and Block Expression of TGFb2 (Abstract #553). in The Twelfth Annual Meeting of the American Society of Gene Therapy. 2009. San Diego, Calif.
45. Page, R. E., et al., Increased expression of the pro-protein convertase furin predicts decreased survival in ovarian cancer. Cell Oncol, 2007. 29(4): p. 289-99.
46. Schalken, J. A., et al., fur gene expression as a discriminating marker for small cell and nonsmall cell lung carcinomas. J Clin Invest, 1987. 80(6): p. 1545-9.
47. Mbikay, M., et al., Comparative analysis of expression of the proprotein convertases furin, PACE4, PC1 and PC2 in human lung tumours. Br J Cancer, 1997. 75(10): p. 1509-14.
48. Cheng, M., et al., Pro-protein convertase gene expression in human breast cancer. Int Cancer, 1997. 71(6): p. 966-71.
49. Bassi, D. E., H. Mahloogi, and A. J. Klein-Szanto, The proprotein convertases furin and PACE4 play a significant role in tumor progression. Mol Carcinog, 2000. 28(2): p. 63-9.
50. Bassi, D. E., et al., Elevated furin expression in aggressive human head and neck tumors and tumor cell lines. Mol Carcinog, 2001. 31(4): p. 224-32.
51. Lopez de Cicco, R., et al., Human carcinoma cell growth and invasiveness is impaired by the propeptide of the ubiquitous proprotein convertase furin. Cancer Res, 2005. 65(10): p. 4162-71.
52. Khatib, A. M., et al., Proprotein convertases in tumor progression and malignancy: novel targets in cancer therapy. Am J Pathol, 2002. 160(6): p. 1921-35.
53. Thomas, G., Furin at the cutting edge: from protein traffic to embryogenesis and disease. Nat Rev Mol Cell Biol, 2002. 3(10): p. 753-66.
54. Pesu, M., et al., T-cell-expressed proprotein convertase furin is essential for maintenance of peripheral immune tolerance. Nature, 2008. 455(7210): p. 246-50.

55. Pesu, M., et al., Proprotein convertase furin is preferentially expressed in T helper 1 cells and regulates interferon gamma. Blood, 2006. 108(3): p. 983-5.
56. Lu, J., et al., TAP-independent presentation of CTL epitopes by Trojan antigens. J Immunol, 2001. 166(12): p. 7063-71.
57. Fogel-Petrovic, M., et al., Physiological concentrations of transforming growth factor beta1 selectively inhibit human dendritic cell function. Int Immunopharmacol, 2007. 7(14): p. 1924-33.
58. Bommireddy, R. and T. Doetschman, TGFbeta 1 and Treg cells: alliance for tolerance. Trends Mol Med, 2007. 13(11): p. 492-501.
59. Henrich, S., et al., The crystal structure of the proprotein processing proteinase furin explains its stringent specificity. Nat Struct Biol, 2003. 10(7): p. 520-6.
60. Pearton, D. J., et al., Proprotein convertase expression and localization in epidermis: evidence for multiple roles and substrates. Exp Dermatol, 2001. 10(3): p. 193-203.
61. Rao, D., Maples, P. B., Senzer, N., Kumar, P., Wang, Z., papper, B. O., Yu, Y., Haddock, C., Tong, A., Nemunaitis, J., Bi-functional shRNA: A novel approach of RNA interference. (submitted), 2009.
62. Matranga, C., et al., Passenger-strand cleavage facilitates assembly of siRNA into Ago2-containing RNAi enzyme complexes. Cell, 2005. 123(4): p. 607-20.
63. Leuschner, P. J., et al., Cleavage of the siRNA passenger strand during RISC assembly in human cells. EMBO Rep, 2006. 7(3): p. 314-20.
64. Rana, S., et al., Stathmin 1: a novel therapeutic target for anticancer activity. Expert Rev Anticancer Ther, 2008. 8(9): p. 1461-70.
65. Azuma-Mukai, A., et al., Characterization of endogenous human Argonautes and their miRNA partners in RNA silencing. Proc Natl Acad Sci USA, 2008. 105(23): p. 7964-9.
66. Jackson, S. A., S. Koduvayur, and S. A. Woodson, Self-splicing of a group I intron reveals partitioning of native and misfolded RNA populations in yeast. RNA, 2006. 12(12): p. 2149-59.
67. Funston, G. M., et al., Expression of heterologous genes in oncolytic adenoviruses using picornaviral 2A sequences that trigger ribosome skipping. J Gen Virol, 2008. 89(Pt 2): p. 389-96.
68. Tong, A. W., et al., Intratumoral injection of INGN 241, a nonreplicating adenovector expressing the melanoma-differentiation associated gene-7 (mda-7/IL24): biologic outcome in advanced cancer patients. Mol Ther, 2005. 11(1): p. 160-72.
69. Hu, X., et al., Characterization of a unique factor-independent variant derived from human factor-dependent TF-1 cells: a transformed event. Leuk Res, 1998. 22(9): p. 817-26.
70. Santoli, D., et al., Synergistic and antagonistic effects of recombinant human interleukin $(IL)_3$, IL-1 alpha, granulocyte and macrophage colony-stimulating factors (G-CSF and M-CSF) on the growth of GM-CSF-dependent leukemic cell lines. J Immunol, 1987. 139(10): p. 3348-54.
71. Romero, P., Current state of vaccine therapies in non-small-cell lung cancer. Clin Lung Cancer, 2008. 9 Suppl 1: p. S28-36.
72. Robinson, J., et al., The European searchable tumour line database. Cancer Immunol Immunother, 2009.
73. http:jura.wi.mit.edu/bioc/siRNAext
74. Kumar, P. J., C. Oxendine, I Nemunaitis, J. Maples, P., TAG Xenograft Vaccine: Xenograft-Expanded Autologous Tumor Vaccine Genetically Modified to Express GM-CSF and Block Production of TGFβ2. BioProcessing Journal, 2009(Spring 2009): p. 30-36.
75. Burghardt, I., et al., Pirfenidone inhibits TGF-beta expression in malignant glioma cells. Biochem Biophys Res Commun, 2007. 354(2): p. 542-7.
76. McMahon, S., M. H. Laprise, and C. M. Dubois, Alternative pathway for the role of furin in tumor cell invasion process. Enhanced MMP-2 levels through bioactive TGF-beta. Exp Cell Res, 2003. 291(2): p. 326-39.
77. Arteaga, C. L., Inhibition of TGFbeta signaling in cancer therapy. Curr Opin Genet Dev, 2006. 16(1): p. 30-7.
78. Constam, D. B., et al., Differential expression of transforming growth factor-beta 1, -beta 2, and -beta 3 by glioblastoma cells, astrocytes, and microglia. J Immunol, 1992. 148(5): p. 1404-10.
79. Eastham, J. A., et al., Transforming growth factor-beta 1: comparative immunohistochemical localization in human primary and metastatic prostate cancer. Lab Invest, 1995. 73(5): p. 628-35.
80. Friedman, E., et al., High levels of transforming growth factor beta 1 correlate with disease progression in human colon cancer. Cancer Epidemiol Biomarkers Prev, 1995. 4(5): p. 549-54.
81. Jakowlew, S. B., et al., Expression of transforming growth factor beta ligand and receptor messenger RNAs in lung cancer cell lines. Cell Growth Differ, 1995. 6(4): p. 465-76.
82. Kong, F. M., et al., Elevated plasma transforming growth factor-beta 1 levels in breast cancer patients decrease after surgical removal of the tumor. Ann Surg, 1995. 222(2): p. 155-62.
83. Yamada, N., et al., Enhanced expression of transforming growth factor-beta and its type-I and type-II receptors in human glioblastoma. Int J Cancer, 1995. 62(4): p. 386-92.
84. Eder, I. E., et al., Transforming growth factors-beta 1 and beta 2 in serum and urine from patients with bladder carcinoma. J Urol, 1996. 156(3): p. 953-7.

What is claimed is:

1. An autologous cell vaccine comprising:
a bishRNAfurin/GMCSF expression vector plasmid, wherein the vector plasmid comprises
a first nucleic acid insert operably linked to a promoter, wherein the first insert encodes a Granulocyte Macrophage Colony Stimulating Factor (GM-CSF) cDNA;
a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference wherein the shRNA incorporates cleavage dependent siRNA and cleavage independent miRNA motifs, wherein the shRNA comprises SEQ ID NO:2; and
one or more optional vaccine adjuvants.

2. The composition of claim 1, wherein the GM-CSF is human.

3. The composition of claim 1, wherein a nucleotide sequence encoding a picornaviral 2A ribosomal skip peptide sequence is intercalated between the first and the second nucleic acid inserts.

4. The composition of claim 1, wherein the promoter is a CMV mammalian promoter.

5. The composition of claim 4, wherein the CMV mammalian promoter contains a CMV IE 5' UTR enhancer sequence and a CMV IE Intron A.

6. An autologous furin-knockdown and Granulocyte Macrophage Colony Stimulating Factor (GM-CSF) augmented (FANG) cancer vaccine composition comprising:
an autologous cancer cell transfected with a vector comprising:
a first nucleic acid insert operably linked to a promoter, wherein the first insert encodes the GM-CSF cDNA; and
a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference wherein the shRNA incorporates cleavage dependent siRNA and cleavage independent miRNA motifs of SEQ ID NO: 2.

7. An autologous cell vaccine composition for cancer treatment by inhibition of furin expression via RNA interference comprising:
a bishRNAfurin/GMCSF expression vector plasmid, wherein the vector plasmid comprises
a first nucleic acid insert operably linked to a promoter, wherein the first insert encodes a Granulocyte Macrophage Colony Stimulating Factor (GM-CSF) cDNA;
a second nucleic acid insert operably linked to the promoter, wherein the second insert encodes one or more bi-functional short hairpin RNAs (shRNAfurin) providing a single targeted site for both a cleavage and a sequestering mechanism of RNA interference, wherein the bi-functional shRNAfurin comprises a first stem-loop structure comprising a complete complementary guide strand and a passenger strand and a second stem-loop structure comprising one or more basepair mismatches of the passenger strand capable of hybridizing to a region of a mRNA transcript encoding furin, wherein the shRNA comprises SEQ ID NO: 2, thereby inhibiting furin expression via RNA interference; and
one or more vaccine adjuvants.

* * * * *